United States Patent
Onuki et al.

(10) Patent No.: US 6,702,863 B1
(45) Date of Patent: Mar. 9, 2004

(54) HAIRDYE COMPOSITION

(75) Inventors: Takeshi Onuki, Tokyo (JP); Mutsumi Noguchi, Tokyo (JP); Joji Mitamura, Tokyo (JP)

(73) Assignee: Lion Corporation, Tokyo (JP)

( * ) Notice: Subject to any disclaimer, the term of this patent is extended or adjusted under 35 U.S.C. 154(b) by 0 days.

(21) Appl. No.: 09/959,962

(22) PCT Filed: Jun. 22, 2000

(86) PCT No.: PCT/JP00/04089

§ 371 (c)(1), (2), (4) Date: Nov. 13, 2001

(87) PCT Pub. No.: WO00/78274

PCT Pub. Date: Dec. 28, 2000

(30) Foreign Application Priority Data

Jun. 22, 1999 (JP) .............................. 11-175169

(51) Int. Cl.⁷ ................................. A61K 7/13
(52) U.S. Cl. ....................... 8/405; 8/401; 8/406; 8/407; 8/409; 8/411
(58) Field of Search .................. 8/401, 405, 406, 8/407, 409, 411

(56) References Cited

U.S. PATENT DOCUMENTS

| | | | |
|---|---|---|---|
| 3,061,432 A | 10/1962 | Menzel et al. ............ | 96/55 |
| 3,251,742 A | 5/1966 | Soloway ................. | 167/88 |
| 3,277,554 A | 10/1966 | Morse .................... | 29/33 |
| 3,419,391 A | 12/1968 | Young .................... | 96/56.5 |
| 3,725,067 A | 4/1973 | Bailey et al. ............ | 96/56.5 |
| 3,907,799 A | 9/1975 | O'Brien et al. .......... | 260/256 |
| 3,926,631 A | 12/1975 | Arai et al. .............. | 96/29 D |
| 3,957,424 A | 5/1976 | Zeffren et al. .......... | 8/10.2 |
| 4,128,425 A | 12/1978 | Greenwald ............... | 96/66 |
| 4,500,630 A | 2/1985 | Sato et al. .............. | 430/386 |
| 4,961,925 A * | 10/1990 | Tsujino et al. .......... | 424/7.02 |
| 5,256,526 A | 10/1993 | Suzuki et al. ........... | 430/383 |
| 5,441,863 A | 8/1995 | Tang et al. .............. | 430/558 |
| 5,457,210 A | 10/1995 | Kim et al. .............. | 548/262.4 |
| 5,667,531 A | 9/1997 | Yaver et al. ............ | 8/901 |
| 5,948,121 A * | 9/1999 | Aaslyng et al. ........ | 8/401 |
| 6,106,579 A * | 8/2000 | Kunz et al. ............. | 8/432 |

FOREIGN PATENT DOCUMENTS

| | | |
|---|---|---|
| DE | DT 2359399 A1 | 6/1975 |
| DE | 3843892 A1 | 6/1990 |
| DE | 4133957 A1 | 4/1993 |
| DE | 19543988 A1 | 5/1997 |

(List continued on next page.)

OTHER PUBLICATIONS

James D. Sullivan, Jr. et al., Biochimica et Biophysica Acta, (1973), vol. 309, pp. 11–22.
Miyoshi Ikawa, Methods in Enzymology, vol. 89, pp. 145–149, (1982).
Vishnu J. Ram et al., Indian Journal of Chemistry, vol. 34B, (Jun. 1995), pp. 514–520.
Nadia S. Ibrahim et al., Arch. Pharm. (Weinheim) vol. 320, (1987), pp. 240–246.
Robert H. Springer et al., J. Med. Chem., (1982), vol. 25, pp. 235–242.
Thomas Novinson et al., J. Med. Chem., vol. 20, pp. 296–299, (1977).
Alexander McKillop et al., HETEROCYCLES, vol. 6, No. 9, 10, (1977), pp. 1355–1360.
Koji Saito et al., Bull. Chem. Soc. Japan, vol. 47, No. 2, (1974), pp. 476–480.
Joseph Bailey, J. Chem. Soc., Perkin, Trans.I, (1977), pp. 2047–20
Mohamed Helmy Elnagdi et al., J.f. Prakt. Chem. vol. 320, No. 4, (1978), pp. 533–538.
Philip Magnus et al., J.A.C.S., vol. 112, (1990), pp. 2465–2468.
Paul Carter et al., J.A.C.S., vol. 109, (1987), pp. 2711–2717.
H. Koopman, Rec. Trav. Chim, vol. 80, (1961), pp. 1075–1083.
Lidia Wyzgowska et al., Acta. Pol. Pharm., vol. 39 (1–3), (1982), pp. 83–88 (w/abstract).
Mohamed Helmi Elnagdi et al., Bull. Chem. Soc. Japan, vol. 46, No. 6, (1973), pp. 1830–1833.
S. Syed Shafi et al., Indian Journal of Heterocyclic Chemistry, vol. 5 (Oct. –Dec. 1995) pp. 135–138.
Ermitas Alcalde et al., J. Heterocyclic Chem., vol. 11, No. 3 (1974) pp. 423–429.
Chem. Ber., vol. 32 (1899) pp. 797–798.
Chem. Ber., vol. 89, (1956) pp. 2550–2555.
Giuliana Cardillo et al., Gazz. Chim. Ital., vol. 96, No. 8–9, (1966), pp. 973–985.
Victor Israel Cohen, J. Heterocycl. Chem., vol. 16, (1979), pp. 13–17.
Mohamed I. Ali et al., J.f. Prakt. Chem., vol. 318, No. 1, (1976), pp. 12–18.
Von Dr. H. Gold, Angew. Chem., vol. 72, No. 24, (1960), pp. 956–959.
(Mrs.) E.J. Browne et al., Triazoles, Part VII, (1962) pp. 5149–5152.
Thomas Kauffman et al., Chem. Berichte, "Metallydrazide (VIII)" (1964) pp. 3436–3443.
Khim. Geterotsilk. Soedin, (1967) pp. 93–96.
Henry K. Foks et al., Acta. Pol. Pharm., vol. 52, No. 5, (1995), pp. 415–420.
Ferenc Korodi et al., Heterocycl. Commun., vol. 1, No. 4, (1995), pp. 297–306.
E. Hannig et al., Pharmazie, vol. 35, No. 4, pp. 231 (1980) (w/abstract).
Eser Ilhan et al., Arch. Parm. (Weinheim), vol. 327, pp. 825–826 (1994) (w/abstract).

Primary Examiner—Yogendra N. Gupta
Assistant Examiner—Eisa Elhilo
(74) Attorney, Agent, or Firm—Birch, Stewart, Kolasch & Birch, LLP

(57) ABSTRACT

A hairdye composition, characterized in that, indoline and/or indoline compound and laccase are compounded.

21 Claims, No Drawings

FOREIGN PATENT DOCUMENTS

| | | |
|---|---|---|
| EP | 0119860 B1 | 9/1984 |
| EP | 0244160 B1 | 11/1987 |
| EP | 0285274 B1 | 10/1988 |
| EP | 0304001 A2 | 2/1989 |
| EP | 0456226 A1 | 11/1991 |
| EP | 0488248 A1 | 6/1992 |
| EP | 0488909 B1 | 6/1992 |
| EP | 0518328 B1 | 12/1992 |
| EP | 0557851 A1 | 9/1993 |
| EP | 0578248 B1 | 1/1994 |
| EP | 0628559 A1 | 12/1994 |
| EP | 0714954 A2 | 6/1996 |
| EP | 1 013 260 A | 6/2000 |
| FR | 2075583 | 10/1971 |
| FR | 2 694 018 A | 1/1994 |
| FR | 2 694 021 A | 1/1994 |
| FR | 2733749 | 11/1996 |
| FR | 2 773 481 A | 7/1999 |
| GB | 1026978 | 4/1966 |
| GB | 1153196 | 5/1969 |
| GB | 1458377 | 12/1976 |
| JP | 47-10400 | 5/1972 |
| JP | 53-32132 A | 3/1978 |
| JP | 58-42045 A | 3/1983 |
| JP | 59-99437 A | 6/1984 |
| JP | 59-162548 A | 9/1984 |
| JP | 59-171956 A | 9/1984 |
| JP | 60-033552 A | 2/1985 |
| JP | 60-043659 A | 3/1985 |
| JP | 60-172982 A | 9/1985 |
| JP | 60-190779 A | 9/1985 |
| JP | 62-279337 A | 12/1987 |
| JP | 63-246313 A | 10/1988 |
| JP | 2-19576 A | 1/1990 |
| JP | 2-238885 A | 9/1990 |
| JP | 5-163124 A | 6/1993 |
| JP | 6-172145 A | 6/1994 |
| JP | 06-236011 A | 8/1994 |
| JP | 07-036159 A | 2/1995 |
| JP | 07-084348 A | 3/1995 |
| JP | 07-092632 A | 4/1995 |
| JP | 07-098489 A | 4/1995 |
| JP | 07-244361 A | 9/1995 |
| JP | 07-325375 A | 12/1995 |
| JP | 8-40857 | 2/1996 |
| WO | WO 94/08969 A1 | 4/1994 |
| WO | WO 94/08970 A1 | 4/1994 |
| WO | WO 99/36046 A1 | 7/1994 |
| WO | WO 94/25574 A1 | 11/1994 |
| WO | WO 92/01046 A1 | 1/1995 |
| WO | WO 95/01772 A1 | 1/1995 |
| WO | WO 95/07988 A1 | 3/1995 |
| WO | WO 95/15144 A1 | 6/1995 |
| WO | WO 95/33836 A1 | 12/1995 |
| WO | WO 95/33837 A1 | 12/1995 |
| WO | WO 96/00290 A1 | 1/1996 |
| WO | WO 96/15765 A1 | 5/1996 |
| WO | WO 97/19998 A1 | 6/1997 |
| WO | WO 99/36034 A1 | 7/1999 |
| WO | WO 99/36035 A1 | 7/1999 |
| WO | WO 99/36036 A1 | 7/1999 |
| WO | WO 99/36037 A1 | 7/1999 |
| WO | WO 99/36038 A1 | 7/1999 |
| WO | WO 99/36039 A1 | 7/1999 |
| WO | WO 99/36040 A1 | 7/1999 |
| WO | WO 99/36041 A1 | 7/1999 |
| WO | WO 99/36042 A1 | 7/1999 |
| WO | WO 99/36043 A1 | 7/1999 |
| WO | WO 99/36044 A1 | 7/1999 |
| WO | WO 99/36045 A1 | 7/1999 |

* cited by examiner

HAIRDYE COMPOSITION

This application is the national phase under 35 U.S.C. §371 of PCT International Application No. PCT/JP00/04089 which has an International filing date of Jun. 22, 2000 which designated the United States of America, the entire contents of which are hereby incorporated by reference.

TECHNICAL FIELD OF THE INVENTION

The present invention relates to a hairdye composition containing indoline and/or indoline compound and laccase and, more particularly, it relates to an oxidative hairdye composition having little skin irritation, a good stability with a lapse of time, an excellent hair-dyeing effect, an excellent usability and particularly an ability of being prepared as a single preparation type.

BACKGROUND ART

Usually, an oxidative hairdye contains an oxidation dye (the first preparation) and an oxidizing agent (the second preparation) and, upon use, they are mixed to react and are applied to hair whereby white hair is dyed. When a commercially available oxidative hairdye is used, there is a risk of causing a rash because p-phenylenediamine, p-aminophenol, etc. compounded in the first preparation are skin-sensitive substances. On the other hand, with regard to the composition for the second preparation, most of it uses hydrogen peroxide as an oxidizing agent and, therefore, there is a possibility of damage of hair and skin.

Under such circumstances, indole compounds and indoline compounds have been proposed as substitutes for the conventional oxidation dyes (Japanese Laid-Open Patent Hei-8/40857) but the present situation is that using only such substances results in poor hair dyeing. On the other hand, as attempts for reducing the damage of hair by hydrogen peroxide, various means using an oxidase has been proposed. Examples of such an art are the use of laccase (U.S. Pat. No. 3,251,742 and Japanese Laid-Open Patent Hei-6/172145), the use of peroxidase (Japanese Laid-Open Patents Sho-47/10400 and Sho-53/32132) and the use of uricase (Japanese Laid-Open Patent Sho-63/246313). However, in most of the art disclosed herein, hydrogen peroxide is added or hair dyeing is conducted by effective utilization of hydrogen peroxide due to the characteristic feature of the enzyme whereby elimination of the problem by hydrogen peroxide is not fundamentally solved. Further, in the case of laccase, due to its unstable property during preservation, when it is compounded in the composition, reaction of oxygen with an oxidation dye in a headspace takes place whereupon insoluble aggregates are formed. Formation of such insoluble aggregates in a product is a very big problem as a hairdye. Accordingly, there is a big problem that it cannot be put on a market as a product unless such insoluble matters are suppressed.

DISCLOSURE OF INVENTION

The present invention has been accomplished under the above-mentioned circumstances and an object of the present invention is to offer an oxidative hairdye composition having little skin sensitivity, a good stability with a lapse of time, an excellent hair dyeing effect and an excellent usability.

In order to achieve the above-mentioned object, the present inventors have conducted an intensive study for achieving the above-mentioned object, found that an oxidative hairdye composition having little skin irritation, an excellent hair dyeing effect, a good stability even by preparing into a single preparation type and an excellent usability can be obtained when indoline and/or indoline compound and laccase are jointly used and have now achieved the present invention.

BEST MODE FOR CARRYING OUT THE INVENTION

When the present invention is illustrated in detail, indoline and/or indoline compound as developer(s) and laccase as an oxidizing agent are compounded in a hairdye composition of the present invention.

Examples of indoline and indoline compound are indoline, 5,6-dihydroxyindoline, N-methyl-5,6-dihydroxyindoline, N-ethyl-5,6-dihydroxyindoline, N-butyl-5,6-dihydroxyindoline, 4-hydroxy-5-methoxyindoline, 6-hydroxy-7-methoxyindoline, 6,7-dihydroxyindoline, 4,5-dihydroxyindoline, 4-methoxy-6-hydroxyindoline and salts thereof and each of them may be used either solely or two or more of them may be used jointly.

The compounding concentration of indoline and/or indoline compound in the composition of the present invention varies depending upon the frequency of use and the dosage form but, usually, it is 0.01–30% (% by weight; hereinafter, % will be used in the same sense) or, preferably, 0.05–20%.

When color change is desired in the hair dye composition of the present invention, a small amount of oxidation dye may be used as a coupler. Known couplers may be used as such an oxidation dye. For example, those which are described in "Standards for Materials for Quasi-Drugs," such as 5-amino-o-cresol, o-aminophenol, m-aminophenol, p-aminophenol, 2,6-diaminopyridine, 5-(2-hydroxyethylamino)-2-methylphenol, N,N-bis(β-hydroxyl)-p-phenylenediamine sulfate, p-nitro-o-phenylenediamine, p-phenylenediamine, m-phenylenediamine, N-phenyl-p-phenylenediamine, resorcinol, 2-hydroxyl-5-nitro-2',4'-diaminoazobenzene sodium sulfate, toluene-2,5-diamine, 5-amino-o-cresol sulfate, p-aminophenol sulfate, o-chloro-p-phenylenediamine sulfate, 4,4'-diaminodiphenylamine sulfate, p-methylaminophenol sulfate, p-phenylenediamine sulfate, m-phenylenediamine sulfate, toluene-2,5-diamine sulfate, 2,4-diaminophenoxyethanol hydrochloride, toluene-2,5-diamine hydrochloride, m-phenylenediamine hydrochloride, 2,4-diaminophenol hydrochloride, 3,3'-iminodiphenol, p-phenylenediamine hydrochloride, N-phenyl-p-phenylenediamine hydrochloride, N-phenyl-p-phenylenediamine acetate, 1,5-dihydroxynaphthalene, toluene-3,4-diamine, p-methylaminophenol, N,N'-bis(4-aminophenyl)-2,5-diamino-1,4-quinonediimine, o-aminophenol sulfate, 2,4-diaminophenyl sulfate and m-aminophenol sulfate, may be used in an appropriate amount either solely or jointly by combining two or more.

Further, direct materials which are frequently used together with such oxidation dyes such as 2-amino-4-nitrophenol, 2-amino-5-nitrophenol, 1-amino-4-methylaminoanthraquinone, nitro-p-phenylenediamine hydrochloride, 1,4-diaminoanthraquinone, nitro-p-phenylenediamine, picramic acid, sodium picramate, 2-amino-5-nitrophenol sulfate, nitro-p-phenylenediamine sulfate, p-nitro-o-phenylenediamine sulfate and p-nitro-m-phenylenediamine sulfate may be used as well.

Such a coupler may be used only when color of the dyed hair is to be changed and, in that case, its compounding concentration in the composition is 0.001–5% or, preferably, 0.005–2%. WO 99/36034, WO 99/36035, WO 99/36036, WO 99/36037, WO 99/36038, WO 99/36039, WO 99/36040, WO 99/36041, WO 99/36042, WO 99/36043, WO 99/36044, WO 99/36045 and WO 99/36046 in the name of L'Oreal discloses different kind of oxidizing dyes (developed substances or oxidation bases) and coupling components (coupling agents) which can also be used according to the present invention and which are hereby incorporated by reference.

The oxidation bases can in particular be selected among para-phenylenediamines, double bases, para-aminophenols, ortho-aminophenols and heterocyclic oxidation bases.

Among the para-phenylenediamines suitable as oxidation bases in the dye compositions according to the invention, the following compounds of the formula (1) and their addition salts with an acid can in particular be mentioned:

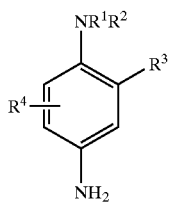

(1)

in which
R$^1$ represents a hydrogen atom, $C_1$–$C_4$-alkyl, $C_1$–$C_4$-monohydroxyalkyl, $C_2$–$C_4$-polyhydroxyalkyl, ($C_1$–$C_4$)alkoxy($C_1$–$C_4$)alkyl, $C_1$–$C_4$-alkyl substituted with a nitrogen-containing group, phenyl or 4'-aminophenyl;
R$^2$ represents a hydrogen atom, $C_1$–$C_4$-alkyl, $C_1$–$C_4$monohydroxyalkyl, $C_2$–$C_4$polyhydroxyalkyl, ($C_1$–$C_4$)alkoxy($C_1$–$C_4$)alkyl or $C_1$–$C_4$alkyl substituted with a nitrogen-containing group;
R$^3$ represents a hydrogen atom, a halogen atom such as chlorine, bromine, iodine or fluorine, $C_1$–$C_4$alkyl, $C_1$–$C_4$monohydroxyalkyl, $C_1$–$C_4$hydroxyalkoxy, $C_1$–$C_4$acetylaminoalkoxy, $C_1$–$C_4$mesylaminoalkoxy or $C_1$–$C_4$carbamoylaminoalkoxy,
R$^4$ represents a hydrogen atom, a halogen atom or $C_1$–$C_4$-alkyl.

Among the nitrogen-containing groups in the above formula (1), amino, mono($C_1$–$C_4$)alkylamino, di($C_1$–$C_4$)alkylamino, tri($C_1$–$C_4$)alkylamino, monohydroxy($C_1$–$C_4$)alkylamino, imidazolinium and ammonium can in particular be mentioned.

More particularly among the para-phenylenediamines of the above formula (1), the following para-phenylenediamines can be mentioned: para-phenylenediamine, paratoluylenediamine, 2-chloro para-phenylenediamine, 2,3-dimethyl para-phenylenediamine, 2,6-dimethyl para-phenylenediamine, 2,6-diethyl para-phenylenediamine, 2,5-dimethyl para-phenylenediamine, N,N-dimethyl para-phenylenediamine, N,N-diethyl para-phenylenediamine, N,N-dipropyl para-phenylenediamine, 4-amino N,N-diethyl 3-methyl aniline, N,N-bis(β-hydroxyethyl) para-phenylenediamine, 4-N,N-bis-(β-hydroxyethyl)amino 2-methyl aniline, 4-N,N-bis-(β-hydroxyethyl)amino 2-chloro aniline, 2-p-hyroxyethyl para-phenylenediamine, 2-fluoro para-phenylenediamine, 2-isopropyl para-phenylenediamine, N-(β-hydroxypropyl) para-phenylenediamine, 2-hydroxymethyl para-phenylenediamine, N,N-dimethyl 3-methyl para-phenylenediamine, N,N-(ethyl, β-hydroxyethyl) para-phenylenediamine, N-(β, γ-dihydroxypropyl) para-phenylenediamine, N-(4'-aminophenyl) para-phenylenediamine, N-phenyl para-phenylene-diamine, 2-β-hydroxyethyloxy para-phenylenediamine, 2-β-acetylaminoethyloxy para-phenylenediamine, N-(β-methoxyethyl) para-phenylenediamine and their addition salts with an acid.

Among the para-phenylenediamines of the above formula (1), the following are especially preferred: para-phenylenediamine, paratoluylenediamine, 2-isopropyl para-phenylenediamine, 2-β-hydroxyethyl para-phenylenediamine, 2-β-hydroxyethyloxy para-phenylenediamine, 2,6-dimethyl para-phenylenediamine, 2,6-diethyl para-phenylenediamine, 2,3-dimethyl para-phenylenediamine, N,N-bis-(β-hydroxyethyl) para-phenylenediamine, 2-chloro para-phenylenediamine, 2-β-acetylaminoethyloxy para-phenylenediamine and their addition salts with an acid.

By double bases is, according to the invention, meant such compositions which include at least two aromatic nuclei carrying amino and/or hydroxyl groups.

Among the double bases suitable as oxidation bases in the dye compositions according to the invention, the compounds of the following formula (2) and their addition salts with an acid can in particular be mentioned:

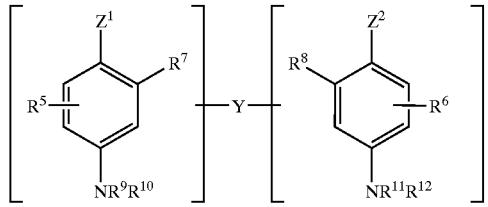

(2)

in which
$Z^1$ and $Z^2$, which are identical or differ, represent a hydroxyl group or —$NH_2$, which can be substituted with a $C_1$–$C_4$alkyl group or with a bridging group Y;
the bridging group Y is a linear or branched alkylene chain with 1 to 14 carbon atoms, which can be interrupted or terminated by one or more nitrogen-containing groups and/or one or more hetero atoms, such as oxygen, sulphur or nitrogen atoms, and optionally be substituted with one or more hydroxyl groups or $C_1$–$C_6$-alkoxy groups;
$R^5$ and $R^6$ represents a hydrogen or halogen atom, $C_1$–$C_4$alkyl, $C_1$–$C_4$mono-hydroxyalkyl, $C_2$–$C_4$polyhydroxyalkyl, $C_1$–$C_4$aminoalkyl or a bridging group Y;
$R^7$, $R^8$, $R^9$, $R^{10}$, $R^{11}$ and $R^{12}$, which are identical or differ, represent a hydrogen atom, a bridging group Y or a $C_1$–$C_4$alkyl group;
whereby it should be understood that the compounds of the formula (2) only include a single bridging group Y per molecule.

Among nitrogen-containing groups of the above formula (2), the following can in particular be mentioned: amino, mono($C_1$–$C_4$)alkylamino, di($C_1$–$C_4$)alkyl-amino, tri($C_1$–$C_4$)alkylamino, monohydroxy($C_1$–$C_4$)alkylamino, imidazolinium and ammonium.

Among the double bases of the above formula (2), the following can more particularly be mentioned: N,N=-bis-(β-hydroxyethyl) N,N'-bis-(4'-aminophenyl) 1,3-diamino propanol, N,N=-bis-(β-hydroxyethyl) N,N=-bis-(4'- aminophenyl) ethylenediamine, N,N=-bis-(4-aminophenyl) tetramethylenediamine, N,N'-bis-(β-hydroxyethyl) N,N'-bis-(4-aminophenyl) tetramethylenediamine, N,N'-bis-(4-methylaminophenyl) tetramethylenediamine, N,N'-bis-(ethyl) N,N'-bis-(4'-amino, 3-methylphenyl) ethylenediamine, 1,8-bis-(2,5-diaminophenoxy)-3,5-dioxaoctane and their addition salts with an acid.

Particularly preferred double bases of the formula (2) are N,N'-bis-(β-hydroxyethyl) N,N'-bis-(4'-aminophenyl) 1,3-diamino propanol, 1,8-bis-(2,5-diamino-phenoxy)-3,5-dioxaoctane or one of their addition salts with an acid.

Among the para-aminophenols suitable as oxidation bases in the dye compositions according to the invention, the compounds of the following formula (3) and their addition salts with an acid can especially be mentioned:

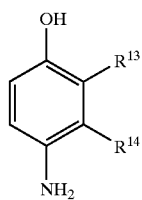

(3)

in which
R$^{13}$ represents a hydrogen or halogen atom, $C_1$–$C_4$alkyl, $C_1$–$C_4$monohydroxyalkyl, ($C_1$–$C_4$)alkoxy($C_1$–$C_4$)alkyl, $C_1$–$C_4$aminoalkyl or ($C_1$–$C_4$)hydroxyalkyl ($C_1$–$C_4$)aminoalkyl, R$^{14}$ represents a hydrogen or halogen atom, $C_1$–$C_4$alkyl, $C_1$–$C_4$monohydroxyalkyl, $C_2$–$C_4$polyhydroxyalkyl, $C_1$–$C_4$aminoalkyl, $C_1$–$C_4$ cyanoalkyl or ($C_1$–$C_4$)alkoxy ($C_1$–$C_4$)alkyl, whereby it should be understood that at least one of the groups R$^{13}$ or R$^{14}$ represents a hydrogen atom.

Among the para-aminophenols of the above formula (3), the following can in particular be mentioned: para-aminophenol, 4-amino 3-methyl phenol, 4-amino 3-fluoro phenol, 4-amino 3-hydroxymethyl phenol, 4-amino 2-methyl phenol, 4-amino 2-hydroxymethyl phenol, 4-amino 2-methoxymethyl phenol, 4-amino 2-aminomethyl phenol, 4-amino 2-(β-hydroxyethyl aminomethyl) phenol, 4-amino 2-fluoro phenol and acid addition salts thereof.

Among the ortho-aminophenols suitable as oxidation bases in the dye compositions according to the invention, the following can in particular be mentioned: 2-amino phenol, 2-amino 5-methyl phenol, 2-amino 6-methyl phenol, 5-acetamido 2-amino phenol and acid addition salts thereof.

Among the heterocyclic bases suitable as oxidation bases in the dye compositions according to the invention, the following can in particular be mentioned: pyridine derivatives, pyrimidine derivatives, pyrazole derivatives, pyrazolo-pyrimidine derivatives and acid addition salts thereof.

Among the pyridine derivatives, the compositions described for instance in the patents GB-PS 1 026 978 and GB-PS 1 153 196 can in particular be mentioned: 2,5-diamino pyridine, 2-(4-methoxyphenyl)amino 3-amino pyridine, 2,3-diamino 6-methoxy pyridine, 2-(β-methoxyethyl)amino 3-amino 6-methoxy pyridine, 3,4-diamino pyridine and the addition salts thereof.

Among the pyrimidine derivatives, the compositions described for instance in the German patent DE 2 359 399 or the Japanese patents JP 88-169 571 and JP 91-333 495 or in the Patent Application WO 96/15765 can in particular be mentioned: 2,4,5,6-tetra-aminopyrimidine, 4-hydroxy 2,5,6-triaminopyrimidine, 2-hydroxy 4,5,6-triaminopyrimidine, 2,4-dihydroxy 5,6-diaminopyrimidine, 2,5,6-triaminopyrimidine and their addition salts with an acid.

Among the pyrazole derivatives, the compounds described for instance in the patents DE 3 843 892 and DE 4 133 957 and in the Patent Applications WO 94/08969, WO 94/08970, FR-A-2 733 749 and DE 195 43 988 can in particular be mentioned: 4,5-diamino 1-methyl pyrazole, 3,4-diamino pyrazole, 4,5-diamino 1-(4'-chlorobenzyl) pyrazole, 4,5-diamino 1,3-dimethyl pyrazole, 4,5-diamino 3-methyl 1-phenyl pyrazole, 4,5-diamino 1-methyl 3-phenyl pyrazole, 4-amino 1,3-dimethyl 5-hydrazino pyrazole, 1-benzyl 4,5-diamino 3-methyl pyrazole, 4,5-diamino 3-tert-butyl 1-methyl pyrazole, 4,5-diamino 1-tert-butyl 3-methyl pyrazole, 4,5-diamino 1-(β-hydroxyethyl) 3-methyl pyrazole, 4,5-diamino 1-ethyl 3-methyl pyrazole, 4,5-diamino 1-ethyl 3-(4'-methoxyphenyl) pyrazole, 4,5-diamino 1-ethyl 3-hydroxymethyl pyrazole, 4,5-diamino 3-hydroxymethyl 1-methyl pyrazole, 4,5-diamino 3-hydroxymethyl 1-isopropyl pyrazole, 4,5-diamino 3-methyl 1-isopropyl pyrazole, 4-amino 5-(2'-aminoethyl) amino 1,3-dimethyl pyrazole, 3,4,5-triamino pyrazole, 1-methyl 3,4,5-triamino pyrazole, 3,5-diamino 1-methyl 4-methylamino pyrazole, 3,5-diamino 4-(β-hydroxyethyl) amino-1-methyl pyrazole and their acid addition salts.

Among the pyrazolo pyrimidine derivatives, the following can in particular be mentioned: the pyrazolo-[1,5-a]-pyrimidines of the formula (4) shown below, their addition salts with an acid or base and their tautomeric forms when a tautomeric equilibrium exists:

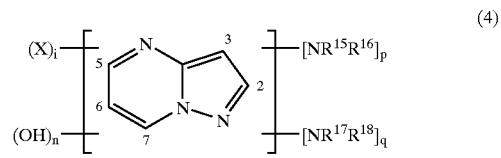

(4)

in which
R$^{15}$, R$^{16}$, R$^{17}$ and R$^{18}$, which are identical or differ, represent a hydrogen atom, $C_1$–$C_4$alkyl, aryl, $C_1$–$C_4$hydroxyalkyl, $C_2$–$C_4$polyhydroxyalkyl, ($C_1$–$C_4$) alkoxy($C_1$–$C_4$)alkyl, $C_1$–$C_4$aminoalkyl (where the amine can be protected by an acetyl, ureido or sulfonyl group), ($C_1$–$C_4$)alkylamino ($C_1$–$C_4$)alkyl, di-[($C_1$–$C_4$) alkyl] amino $C_1$–$C_4$alkyl (where the dialkyl groups can form a carbon ring or a heterocyclic ring with 5 or 6 members), hydroxy-$C_1$–$C_4$alkyl or di-[hydroxy ($C_1$–$C_4$)alkyl]-amino $C_1$–$C_4$alkyl;

the groups X, which are identical or differ, represent a hydrogen atom, $C_1$–$C_4$alkyl, aryl, $C_1$–$C_4$hydroxyalkyl, $c_2$-$c_4$polyhydroxyalkyl, amino $C_1$–$C_4$alkyl, ($C_1$–$C_4$) alkyl($C_1$–$C_4$)aminoalkyl, di-[($C_1$–$C_4$)alkyl] amino$C_1$–$C_4$alkyl (where the dialkyl groups can form a carbon ring or a heterocyclic ring with 5 or 6 members), hydroxy ($C_1$–$C_4$)alkyl or di-[hydroxy($C_1$–$C_4$)alkyl] amino-$C_1$–$C_4$alkyl, amino, $C_1$–$C_4$alkyl or di-[($C_1$–$C_4$) alkyl]-amino, a halogen atom, a carboxylic acid group or a sulfonic acid group;

i is 0, 1, 2 or 3;
p is 0 or 1;
q is 0 or 1;
n is 0 or 1;
with the proviso that
the sum p+q differs from 0;

when p+q is 2, n has the value 0, and the groups $NR^{15}R^{16}$ and $NR^{17}R^{18}$ occupy the positions (2,3); (5,6); (6,7); (3,5) or (3,7);

when p+q is 1, n has the value 1, and the group $NR^{15}R^{16}$ (or $NR^{17}R^{18}$) and the group OH occupy the positions (2,3); (5,6); (6,7); (3,5) or (3,7).

When the pyrazolo-[1,5-a]-pyrimidines of the above formula (4) are such which include a hydroxyl group in one of the positions 2, 5 or 7 in the α-position to a nitrogen atom, a tautomeric equilibrium exists which for instance can be indicated by the following reaction scheme.

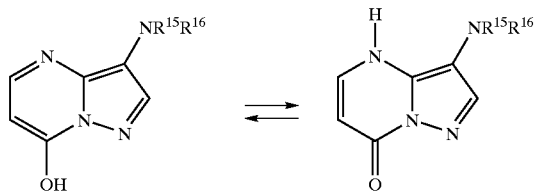

Among the pyrazolo-[1,5-a]-pyrimidines of the above formula (4), the following can be mentioned in particular:

pyrazolo-[1,5-a]-pyrimidine-3,7-diamine;
2,5-dimethyl pyrazolo-[1,5-a]-pyrimidine-3,7-diamine;
pyrazolo-[1,5-a]-pyrimidine-3,5-diamine;
2,7-dimethyl pyrazolo-[1,5-a]-pyrimidine-3,5-diamine;
2,73-amino pyrazolo-[1,5-a]-pyrimidine-7-ol;
3-amino pyrazolo-[1,5-a]-pyrimidine-5-ol;
2-(3-amino pyrazolo-[1,5-a]-pyrimidine-7-ylamino)-ethanol;
2-(7-amino pyrazolo-[1,5-a]-pyrimidine-3-ylamino)-ethanol;
2-[(3-amino-pyrazolo[1,5-a]pyrimidine-7-yl)-(2-hydroxy-ethyl)-amino]ethanol;
2-[(7-amino-pyrazolo[1,5-a]pyrimidine-3-yl)-(2-hydroxy-ethyl)-amino]ethanol;
5,6-dimethyl pyrazolo-[1,5-a]-pyrimidine-3,7-diamine;
2,6-dimethyl pyrazolo-[1,5-a]-pyrimidine-3,7-diamine;
2,5, N 7, N 7-tetramethyl pyrazolo-[1,5-a]-pyrimidine-3, 7-diamine; and their addition salts and tautomeric forms, provided a tautomeric equilibrium exists.

The pyrazolo-[1,5-a]-pyrimidines of the above formula (4) can be prepared by way of cyclisation of an aminopyrazole according to the syntheses described in the following references:

EP 628559 BEIERSDORF-LILLY
R. Vishdu, H. Navedul, Indian J. Chem., 34b (6), 514, 1995.
N. S. Ibrahim, K. U. Sadek, F. A. Abdel-Al, Arch. Pharm., 320, 240, 1987.
R. H. Springer, M. B. Scholten, D. E. O'Brien, T. Novinson, J. P. Miller, R. K. Robins, J. Med. Chem., 25, 235, 1982.
T. Novinson, R. K. Robins, T. R. Matthews, J. Med. Chem., 20, 296, 1977.
US 3907799 ICN PHARMACEUTICAL The pyrazolo-[1,5-a]-pyrimidines of the above formula (4) can furthermore be produced by cyclisation from a hydrazine according to the syntheses described in the following references:

A. McKillop, R. J. Kobilecki, Heterocycles, 6(9), 1355, 1977.
E. Alcade, J. DeMendoza, J. M. Marcia-Marquina, C. Almera, J. Elguero, J. Heterocyclic Chem., 11(3), 423, 1974.
K. Saito, I. Hori, M. Higarashi, H. Midorikawa, Bull. Chem. Soc. Japan, 47(2), 476, 1974.

The oxidation base or bases represent preferably between approximately 0.0005% and approximately 12% by weight of the total weight of the dye composition according to the invention, especially between approximately 0.005% and approximately 6% by weight.

The coupling agent or coupling agents suitable in the ready-to-use dye compositions according to the invention are such which are conventionally used in oxidation dye composition, viz. metaphenylene diamines, metaaminophenols, metadiphenols, heterocyclic coupling agents and their addition salts with an acid.

These coupling agents can especially be selected among 2-methyl-5-amino-phenol, 5-N-(β-hydroxyethyl)-amino-2-methyl-phenol, 3-amino-phenol, 1,3-dihydroxybenzene, 1,3-dihydroxy-2-methyl-benzene, 4-chloro-1,3-dihydroxy-benzene, 2,4-diamino-1-(β-hydroxyethyloxy)-benzene, 2-amino-4-(β-hydroxyethylamino)-1-methoxy-benzene, 1,3-diamino-benzene, 1,3-bis-(2,4-diaminophenoxy)-propane, sesamol, α-naphtol, 6-hydroxy-indole, 4-hydroxy-indole, 4-hydroxy-N-methyl-indole, 6-hydroxy-indolin, 2,6-dihydroxy-4-methyl-pyridine, 1-H-3-methyl-pyrazole-5-on, 1-phenyl-3-methyl-pyrazole-5-one, 2,6-dimethyl-pyrazolo-[1,5-b]-1,2,4-triazole, 2,6-dimethyl-[3,2-c]-1,2,4-triazole, 6-methyl-pyrazolo-[1,5-a]-benzimidazole and acid addition salts thereof.

The meta-aminophenol or meta-aminophenols applicable as coupling agents in the ready-to-use dye composition according to the invention is/are preferably selected from compounds of the following formula (5) and acid addition salts thereof:

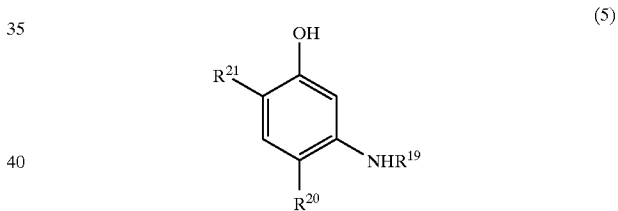

in which $R^{19}$ represents a hydrogen atom, $C_1$–$C_4$-alkyl, $C_1$–$C_4$monohydroxyalkyl or $C_2$–$C_4$polyhydroxyalkyl, $R^{20}$ represents a hydrogen atom, $C_1$–$C_4$alkyl, $C_1$–$C_4$alkoxy or a halogen atom selected from chlorine, bromine and fluorine, $R^{21}$ represents a hydrogen atom, $C_1$–$C_4$alkyl, $C_1$–$C_4$alkoxy, $C_1$–$C_4$mono-hydroxyalkyl, $C_2$–$C_4$polyhydroxyalkyl, $C_1$–$C_4$monohydroxyalkoxy or $C_2$–$C_4$poly-hydroxyalkoxy.

Among the meta-aminophenols of the above formula (5), the following can be mentioned in particular: meta-aminophenol, 5-amino-2-methoxy phenol, 5-amino-2-(β-hydroxyethyloxy)-phenol, 5-amino-2-methyl phenol, 5-N-(β-hydroxyethyl)amino-2-methyl phenol, 5-N-(β-hydroxyethyl)amino-4-methoxy-2-methyl phenol, 5-amino-4-methoxy-2-methyl phenol, 5-amino-4-chloro-2-methyl phenol, 5-amino-2,4-dimethoxy phenol, 5-(γ-hydroxypropylamino)-2-methyl phenol and acid addition salts thereof.

The meta-phenylenediamine or meta-phenylenediamines applicable as coupling agents in the ready-to-use dye composition according to the invention is/are preferably selected from compounds of the following formula (6) and acid addition salts thereof:

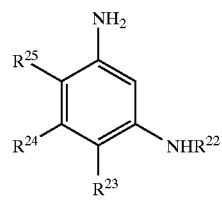

(6)

in which
R$^{22}$ represents a hydrogen atom, C$_1$–C$_4$alkyl, C$_1$–C$_4$monohydroxyalkyl or C$_2$–C$_4$polyhydroxyalkyl;
R$^{23}$ and R$^{24}$, which are identical or differ, each represents a hydrogen atom, C$_1$–C$_4$alkyl, C$_1$–C$_4$monohydroxyalkoxy or C$_2$–C$_4$polyhydroxyalkoxy;
R$^{25}$ represents a hydrogen atom, C$_1$–C$_4$alkoxy, C$_1$–C$_4$aminoalkoxy, C$_1$–C$_4$mono-hydroxyalkoxy, C$_2$–C$_4$polyhydroxyalkoxy or 2,4-diaminophenoxyalkoxy.

Among the meta-phenylenediamines of the above formula (6), the following can in particular be mentioned: 2,4-diamino-benzene, 3,5-diamino-1-ethyl-2-methoxybenzene, 3,5-diamino-2-methoxy-1-methyl benzene, 2,4-diamino-1-ethoxybenzene, 1,3-bis-(2,4-diaminophenoxy) propane, bis-(2,4-diaminophenoxy)-methane, 1-(β-aminoethyloxy)-2,4-diamino-benzene, 2-amino-1-(β-hydroxy-ethyloxy)-4-methylamino-benzene, 2,4-diamino-1-ethoxy 5-methyl-benzene, 2,4-diamino-5-(β-hydroxyethyloxy)-1-methylbenzene, 2,4-diamino-1-(β,γ-dihydroxy-propyloxy) benzene, 2,4-diamino-1-(β-hydroxyethyloxy)-benzene, 2-amino-4-N-(β-hydroxyethyl)-amino-1-methoxy-benzene and acid addition salts thereof.

The meta-diphenol or meta-diphenols applicable as coupling agents in the ready-to-use dye composition according to the invention is/are preferably selected from the compounds of the following formula (7) and acid addition salts thereof:

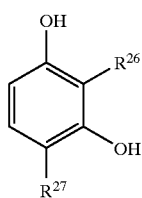

(7)

in which
R$^{26}$ and R$^{27}$, which are identical or differ, each represents a hydrogen atom, C$_1$–C$_4$alkyl or a halogen atom selected from chlorine, bromine and fluorine.

Among the meta-diphenols of the above formula (7), the following can in particular be mentioned: 1,3-dihydroxy-benzene, 2-methyl-1,3-dihydroxy-benzene, 4-chloro-1,3-dihydroxy-benzene, 2-chloro-1,3-dihydroxybenzene, and acid addition salts thereof.

Among the heterocyclic coupling agents applicable in the ready-to-use dye composition according to the invention, derivatives of benzimidazole, derivatives of benzomorpholine, derivatives of sesamol, pyrazolo-azol derivatives, pyrrolo-azole derivatives, imidazolo-azole derivatives, pyrazolo-pyrimidine derivatives, derivatives of pyrazoline-3,5-diones, pyrrolo-[3,2-d]oxazole derivatives, pyrazolo-[3,4-d]-thiazole derivatives, thiazolo-azole S-oxide derivatives, thiazolo-azole S,S-dioxide derivatives and their addition salts with an acid can in particular be mentioned.

Among the benzimidazole derivatives applicable as heterocyclic coupling agents in the dye composition according to the invention, the compounds of the following formula (I) and their acid addition salts can in particular be mentioned:

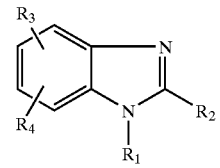

(I)

in which:
R$_1$ represents a hydrogen atom or C$_1$–C$_4$-alkyl,
R$_2$ represents a hydrogen atom, C$_1$–C$_4$alkyl or phenyl,
R$_3$ represents a hydroxyl, amino or methoxy group,
R$_4$ represents a hydrogen atom, a hydroxyl group, a methoxy group or C$_1$–C$_4$alkyl group,
with the proviso that:
when R$_3$ is an amino group, it is in position 4,
when R$_3$ is in position 4, R$_4$ is in position 7,
when R$_3$ is in position 5, R$_4$ is in position 6.

Among the benzimidazole derivatives of the above formula (I), the following can in particular be mentioned: 4-hydroxy benzimidazole, 4-amino benzimidazole, 4-hydroxy-7-methyl benzimidazole, 4-hydroxy-2-methyl benzimidazole, 1-butyl-4-hydroxy benzimidazole, 4-amino-2-methyl benzimidazole, 5,6-dihydroxy benzimidazole, 5-hydroxy-6-methoxy benzimidazole, 4,7-dihydroxy benzimidazole, 4,7-dihydroxy-1-methyl benzimidazole, 4,7-dimethoxy benzimidazole, 5,6-dihydroxy-1-methyl benzimidazole, 5,6-dihydroxy-2-methyl benzimidazole, 5,6-dimethoxy benzimidazole and their addition salts with an acid.

Among the benzomorpholine derivatives applicable as heterocyclic coupling agents in the ready-to-use dye composition according to the invention, the compounds of the following formula (II) and their addition salts with an acid can in particular be mentioned:

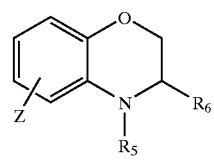

(II)

in which
R$_5$ and R$_6$, which are identical or differ, each represents a hydrogen atom or C$_1$–C$_4$-alkyl, and
Z represents a hydroxyl group or an amino group.

Among the benzomorpholine derivatives of the above formula (II) the following can in particular be mentioned: 6-hydroxy 1,4-benzomorpholine, N-methyl 6-hydroxy 1,4-benzomorpholine, 6-amino 1,4-benzomorpholine and their acid addition salts.

Among the derivatives of sesamol applicable as heterocyclic coupling agents in the ready-to-use dye composition according to the invention, the compounds of the following formula (III) and their addition salts with an acid can in particular be mentioned:

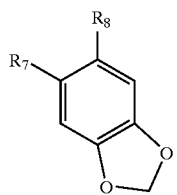

(III)

in which

R$_7$ represents a hydroxyl group, an amino group, a C$_1$–C$_4$-alkylamino group, a C$_1$–C$_4$monohydroxyalkylamino group or a C$_2$–C$_4$polyhydroxyalkylamino group, R$_8$ represents a hydrogen atom, a halogen atom or a C$_1$–C$_4$alkoxy group.

Among the derivatives of sesamol of the above formula (III), the following can in particular be mentioned: 2-bromo 4,5-methylenedioxy phenol, 2-methoxy 4,5-methylenedioxy aniline, 2-(β-hydroxyethyl)amino 4,5-methylenedioxy benzene and their acid addition salts.

Among the pyrazolo-azole derivatives applicable as heterocyclic coupling agents in the ready-to-use dye composition according to the invention, the compounds can in particular be mentioned which are described in the following Patents and Patent Applications: FR 2 075 583, EP-A-119 860, EP-A-285 274, EP-A-244 160, EP-A-578 248, GB 1 458 377, U.S. Pat. No. 3,277,554, U.S. Pat. No. 3,419,391, U.S. Pat. No. 3,061,432, U.S. Pat. No. 4,500,630, U.S. Pat. No. 3,725,067, U.S. Pat. No. 3,926,631, U.S. Pat. No. 5,457,210, JP 84/99437, JP 83/42045, JP 84/162548, JP 84/171956, JP 85/33552, JP 85/43659, JP 85/172982, JP 85/190779 as well in the following publications: Chem. Ber. 32, 797, (1899), Chem. Ber. 89, 2550, (1956), J. Chem. Soc. Perkin trans I, 2047, (1977), J. Prakt. Chem., 320, 533, (1978), the subject matter of which constitute an integrated part of the present application.

As the pyrazolo-azole derivatives, the following can in particular be mentioned:

2-methyl pyrazolo[1,5-b]-1,2,4-triazole, 2-ethyl pyrazolo[1,5-b]-1,2,4-triazole, 2-isopropyl pyrazolo[1,5-b]-1,2,4-triazole, 2-phenyl pyrazolo[1,5-b]-1,2,4-triazole, 2,6-dimethyl pyrazolo[1,5-b]-1,2,4-triazole, 7-chloro-2,6-dimethylpyrazolo[1,5-b]-1,2,4-triazole, 3,6-dimethyl-pyrazolo[3,2-c]-1,2,4-triazole, 6-phenyl-3-methylthio- pyrazolo[3,2-c]-1,2,4-triazole, 6-amino-pyrazolo[1,5-a]benzimidazole, and their addition salts with an acid.

Among the pyrrolo-azole derivatives applicable as heterocyclic coupling agents in the ready-to-use dye composition according to the invention, the compounds can in particular be mentioned which are described in the following Patents and Patent Applications: U.S. Pat. No. 5,256,526, EP-A-557 851, EP-A-578 248, EP-A-518 238, EP-A-456 226, EP-A-488 909, EP-A-488 248 and in the following publications:

D. R. Liljegren Ber. 1964, 3436;

E. J. Browne, J.C.S., 1962, 5149;

P. Magnus, J.A.C.S., 1990, 112, 2465;

P. Magnus, J.A.C.S., 1987, 109, 2711;

Angew. Chem. 1960, 72, 956;

and Rec. Trav. Chim. 1961, 80, 1075, the subject matter of which constitute an integrated part of the present application.

As the pyrazolo-azole derivatives, the following can in particular be mentioned:

5-cyano-4-ethoxycarbonyl-8-methyl pyrrolo [1,2-b]-1,2,4-triazole, 5-cyano-8-methyl-4-phenyl pyrrolo [1,2-b]-1,2,4-triazole, 7-amido-6-ethoxycarbonyl pyrrolo [1,2-a]-benzimidazole, and their addition salts with an acid.

Among the imidazolo-azole derivatives applicable as heterocyclic coupling agents in the ready-to-use dye composition according to the invention, the compounds can in particular be mentioned which are described in the following Patents and Patent Applications: U.S. Pat. No. 5,441,863, JP 62-279 337, JP 06-236 011 and JP 07-092 632, the subject matter of which constitute an integrated part of the present application.

As the imidazolo-azole derivatives, the following can in particular be mentioned:

7,8-dicyano-imidazolo-[3,2-a]-imidazole, 7,8-dicyano-4-methyl-imidazolo -[3,2-a]-imidazole, and their addition salts with an acid.

Among the pyrazolo-pyrimidine derivatives applicable as heterocyclic coupling agents in the ready-to-use dye composition according to the invention, the compounds can in particular be mentioned which are described in the following Patent Application: EP-A-304-001, the subject matter of which constitute an integrated part of the present application.

As the pyrazolo-pyrimidine derivatives, the following can in particular be mentioned:

pyrazolo-[1,5-a]-pyrimidine-7-one, 2,5-dimethyl pyrazolo [1,5-a] pyrimidine-7-one, 2-methyl-6-ethoxycarbonyl pyrazolo [1,5-a] pyrimidine-7-one, 2-methyl-5-methoxymethyl pyrazolo [1,5-a] pyrimidine-7-one, 2-tert-butyl-5-trifluoromethyl pyrazolo [1,5-a] pyrimidine-7-one, 2,7-dimethyl pyrazolo [1,5-a] pyrimidine-5-one, and their addition salts with an acid.

Among the pyrazoline-3,5-diones derivatives applicable as heterocyclic coupling agents in the ready-to-use dye composition according to the invention, the compounds can in particular be mentioned which are described in the following Patents and Patent Applications: JP 07-036159, JP 07-084348 and U.S. Pat. No. 4,128,425, and in the following publications:

L. WYZGOWSKA, Acta. Pol. Pharm. 1982, 39 (1–3), 83.

E. HANNIG, Pharmazie, 1980, 35 (4), 231

M. H. ELNAGDI, Bull. Chem. Soc. Jap., 46(6), 1830, 1973

G. CARDILLO, Gazz. Chim. Ital. 1966, 96, (8–9), 973, the subject matter of which constitute an integrated part of the present application.

As the derivatives of pyrazolin-3,5-diones, the following can in particular be mentioned:

5 1,2-diphenyl pyrazoline-3,5-dione, 1,2-diethyl pyrazoline-3,5-dione, and their addition salts with an acid.

Among the pyrrolo-[3, 2-d]-oxazole derivatives applicable as heterocyclic coupling agents in the ready-to-use dye composition according to the invention, the compounds can in particular be mentioned which are described in the Patent Application JP 07-325 375, the subject matter of which constitute an integrated part of the present application.

Among the pyrazolo-[3,4-d]-thiazole derivatives applicable as heterocyclic coupling agents in the ready-to-use dye composition according to the invention, the compounds can in particular be mentioned which are described in the Patent Application JP 07-244 361 and in J. Heterocycl. Chem. 16, 13, (1979).

Among the thiazolo-azole S-oxide derivatives and thiazolo-azole S,S-dioxide derivatives applicable as heterocyclic coupling agents in the ready-to-use dye composition according to the invention, the compounds can in particular be mentioned which are described in the following documents:

JP 07-098 489;
Khim. Geterotsikl. Soedin, 1967, p. 93;
J. Prakt. Chem., 318, 1976, p. 12;
Indian J. Heterocycl. Chem. 1995, 5(2), p. 135;
Acta. Pol. Pharm. 1995, 52(5), 415;
Heterocycl. Commun. 1995, 1(4), 297;
Arch. Pharm. (Weinheim, Ger.), 1994, 327(12), 825.

These coupling agents constitute preferably between approximately 0.0001% and approximately 10% by weight of the ready-to-use dye composition, especially between approximately 0.005% and approximately 5% by weight.

The cationic direct dye(s) applicable in the ready-to-use dye composition according to the invention is/are preferably selected among cationic amino-anthraquinone dyes, cationic mono or di-azo dyes and cationic naphtoquinone dyes.

Examples of the above are especially[8-[(p-aminophenyl)azo]-7-hydroxy-2-naphtyl]trimethylammonium chloride (also called Basic Brown 16 or Arianor Mahogany 306002 in Color Index), 3-[(4-amino-6-bromo-5,8-dihydro-1-hydroxy-8-imino-5-oxo-2-naphtalenyl)amino]-N,N,N-trimethyl-benzeneaminium chloride (also called Basic Blue 99 or Arianor Steel Blue 306004 in Color Index), 7-hydroxy-8-[(2-methoxyphenyl)azo]-N,N,N-trimethyl-2-naphtaleneaminium chloride (also called Basic Red 76 or Arianor Madder Red in Color Index), [8-[(4-amino-2-nitrophenyl)azo]-7-hydroxy-2-naphtyl]trimethylammonium chloride (also called Basic Brown 17 or Arianor Sienna Brown 306001 in Color Index) and 3-[(4,5-dihydro-3-methyl-5-oxo-1-phenyl-1H-pyrazol-4-yl)azo]-N,N,N-trimethyl-benzenaminium chloride (also called Basic Yellow 57 or Arianor Straw Yellow 306005 in Color Index).

The cationic direct dye(s) can furthermore be selected among:

a) Compounds of the formula (V):

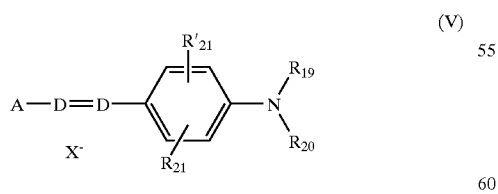

in which

D represents a nitrogen atom or a group —CH, $R_{19}$ and $R_{20}$, which are identical or differ, each represents a hydrogen atom, a $C_1$–$C_4$alkyl group, which can be substituted with one of the groups —CN, —OH or —NH$_2$ or together with a carbon atom in the benzene ring form an optionally oxygen-containing or nitrogen-containing heterocyclic group, which can be substituted with one or more $C_1$–$C_4$alkyl groups; or a 4'-aminophenyl group, $R_{21}$ and $R'_{21}$, which are identical or differ, each represents a hydrogen atom or a halogen atom selected from chlorine, bromine, iodine and fluorine, cyano, $C_1$–$C_4$-alkoxy or acetyloxy, $X^-$ represents an anion, preferably selected from chloride, methylsulphate and acetate, A represents a group selected from the following structures A1–A19:

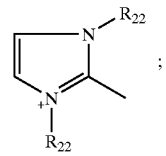

A1

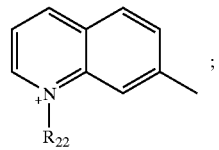

A2

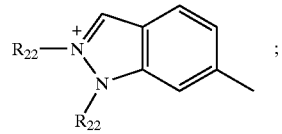

A3

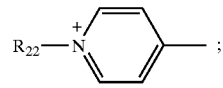

A4

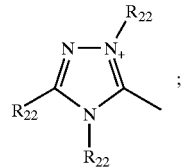

A5

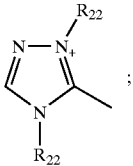

A6

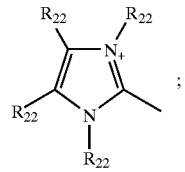

A7

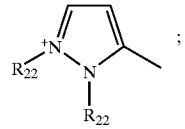

A8

-continued

A9 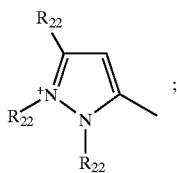

A10 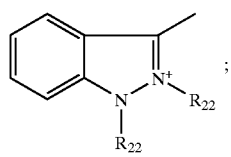

A11 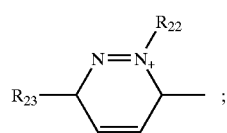

A12 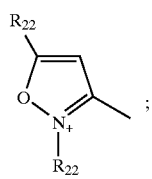

A13 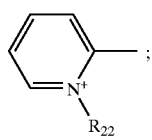

A14 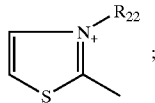

A15 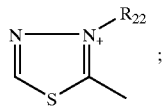

A16 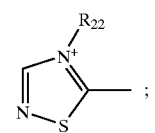

A17 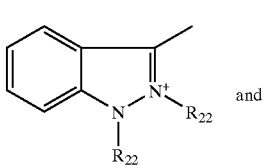

-continued

A19 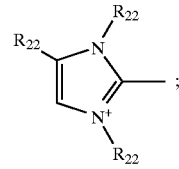

wherein $R_{22}$ represents a $C_1$–$C_4$alkyl group, which can be substituted with a hydroxyl group, and $R_{23}$ represents a $C_1$–$C_4$alkoxy group;

b) compositions of the formula (VI):

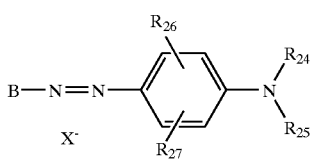

(VI)

in which $R_{24}$ represents a hydrogen atom or a $C_1$–$C_4$alkyl group, $R_{25}$ represents a hydrogen atom, an alkyl group, which can be substituted with a group —CN or with an amino group, or 4'-aminophenyl, or $R_{25}$ represents together with $R_{24}$ an optionally oxygen and/or nitrogen-containing heterocyclic group, which can be substituted with a $C_1$–$C_4$alkyl group, $R_{26}$ and $R_{27}$, which are identical or differ, represent a hydrogen atom, a halogen atom such as bromine, chlorine, iodine or fluorine, $C_1$–$C_4$alkyl, $C_1$–$C_4$alkoxy or the group —CN, $X^-$ represents an anion, preferably selected from chloride, methylsulphate and acetate, B represents a group selected from the following structures B1–B6:

B1 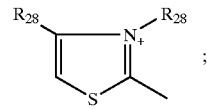

B2 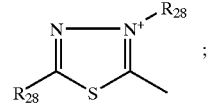

B3 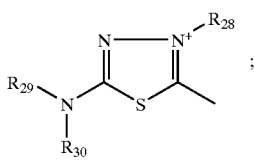

B4 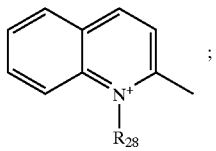

and A18

-continued

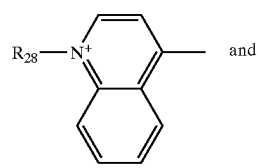
B5 and

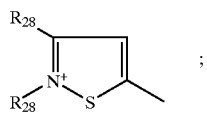
B6 in which $R_{28}$ represents a $C_1$–$C_4$alkyl group, and $R_{29}$ and $R_{30}$, which are identical or differ, each represents a hydrogen atom or a $C_1$–$C_4$alkyl group;

c) compounds of the following formulae (VII) and (VII'):

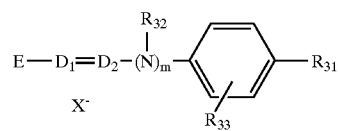
(VII)

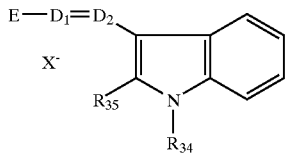
(VII')

in which $R_{31}$ represents a hydrogen atom, a $C_1$–$C_4$alkoxy group, a halogenatom such as bromine, chlorine, iodine or fluorine, or an amino group, $R_{32}$ represents a hydrogen atom or a $C_1$–$C_4$alkyl group, or $R_{32}$ together with a carbon atom in the benzene ring forms a heterocyclic group, which optionally includes an oxygen atom and/or is substituted with one or more $C_1$–$C_4$alkyl groups, $R_{33}$ represents a hydrogen atom or a halogen atom such as bromine, chlorine, iodine or fluorine, $R_{34}$ and $R_{35}$, which are identical or differ, each represents a hydrogen atom or a $C_1$–$C_4$alkyl group, $D_1$ and $D_2$, which are identical or differ, represent a nitrogen atom or a group —CH, m=0 or 1, whereby it should be understood that when $R_{31}$ represents a non-substituted amino group, $D_1$ and $D_2$ represent simultaneously a group —CH, and m=0, $X^-$ represents an anion, preferably selected from chloride, methylsulphate and acetate, E represents a group selected from the following structures E1–E8:

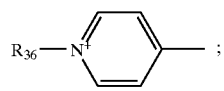
E1

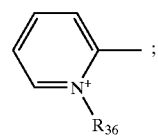
E2

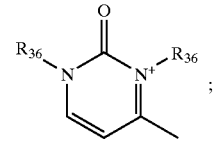
E3

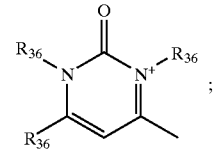
E4

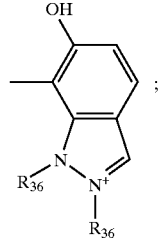
E5

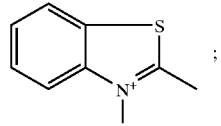
E6

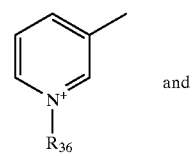
E7 and

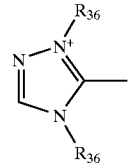
E8 in which $R_{36}$ represents a $C_1$–$C_4$alkyl group;
when m=0 and $D_1$ represents a nitrogen atom, E can also represent a group with the following structure E9:

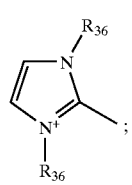
E9 in which $R_{36}$ represents a $C_1$–$C_4$alkyl group.

The cationic direct dyes of the formulae (V), (VI), (VII) and (VII'), which are applicable in the ready-to-use dye compositions according to the invention, are compositions known per se, which are described for instance in the Patent Applications WO 95/01772, WO 95/15144 and EP-A-0 714 954.
Among the cationic direct dyes of the formula (V), which are applicable in the ready-to-use dye compositions according to the invention, the compounds of the following structures (V1) to (V52) can in particular be mentioned:
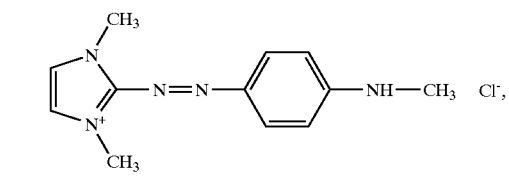
(V1)
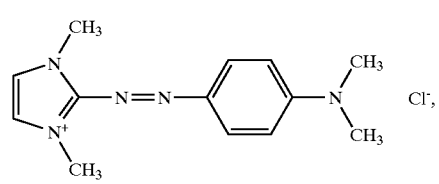
(V2)
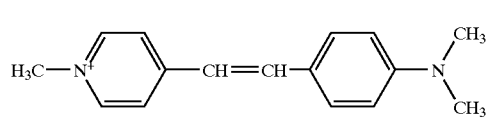
(V3)
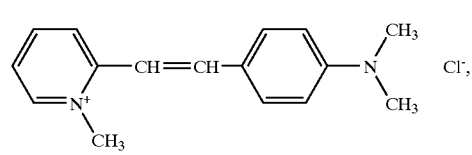
(V4)
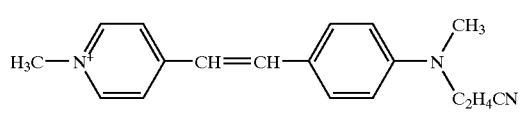
(V5)
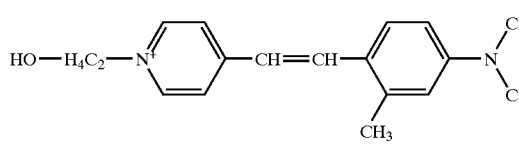
(V6)
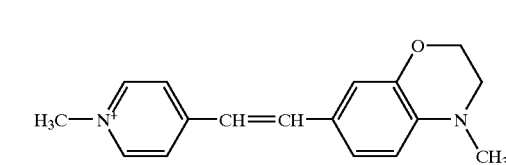
(V7)
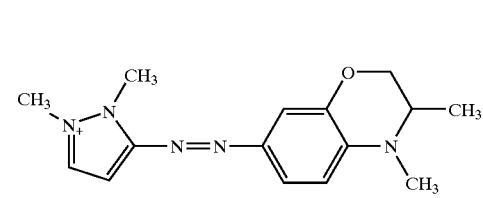
(V8)
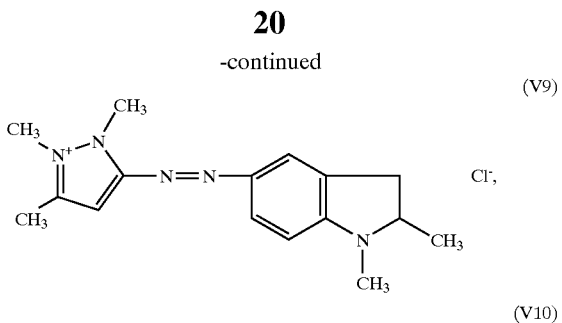
(V9)
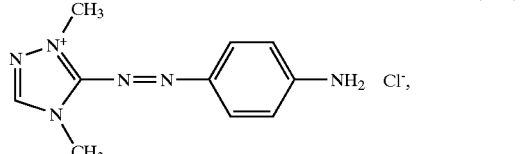
(V10)
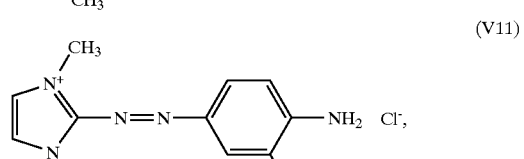
(V11)
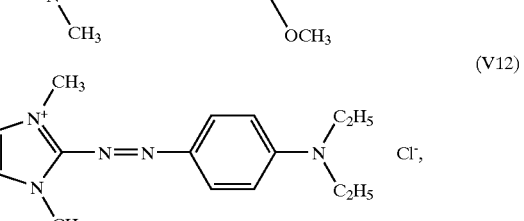
(V12)
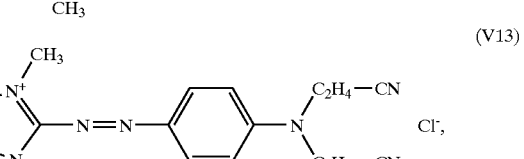
(V13)
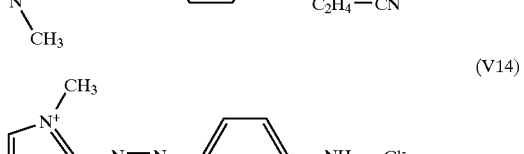
(V14)
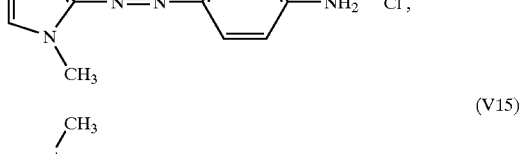
(V15)
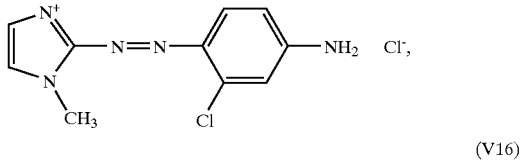
(V16)
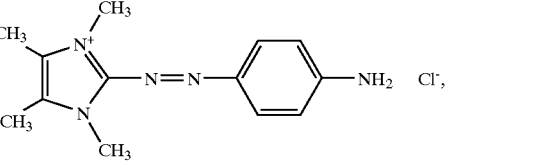
(V17)

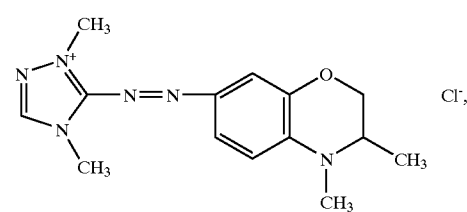 (V18)
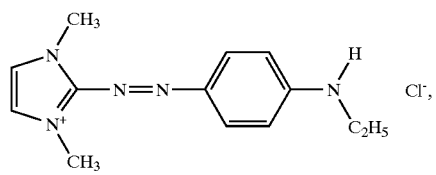 (V19)
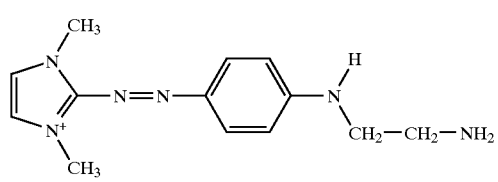 (V20)
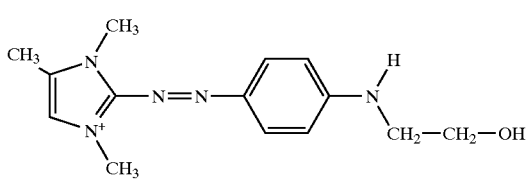 (V21)
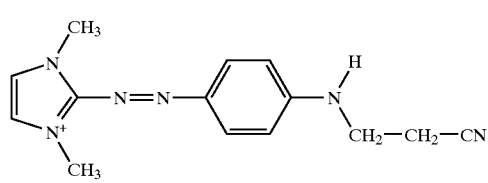 (V22)
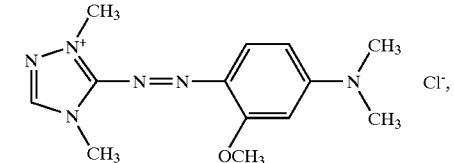 (V23)
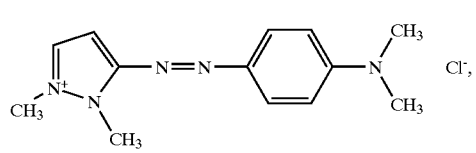 (V24)
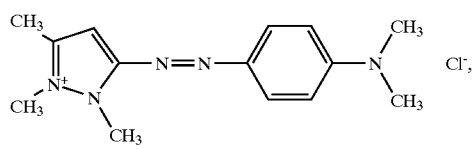 (V25)
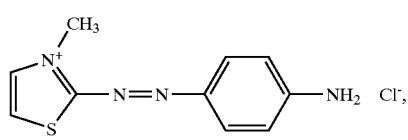 (V26)
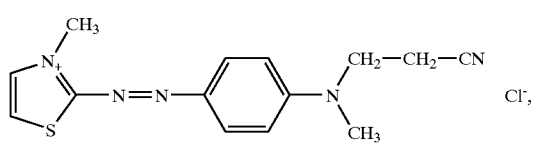 (V27)
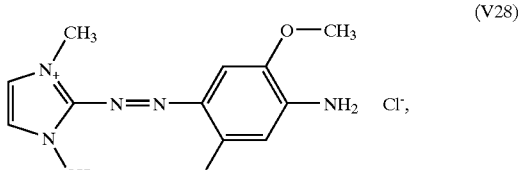 (V28)
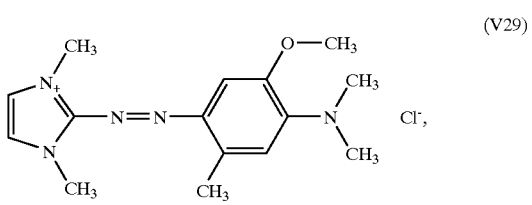 (V29)
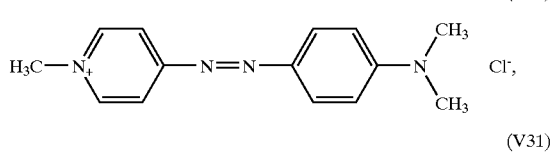 (V30)
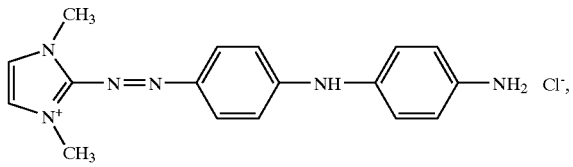 (V31)
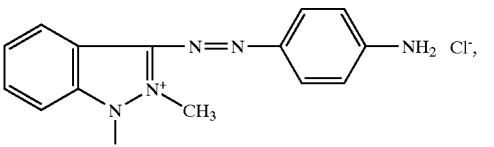 (V32)
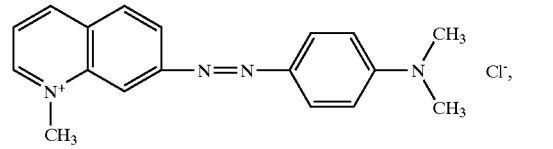 (V33)
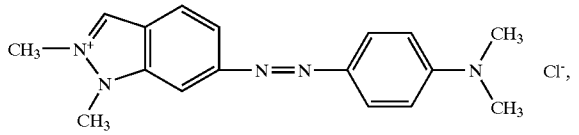 (V34)
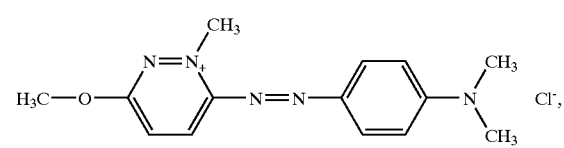 (V35)

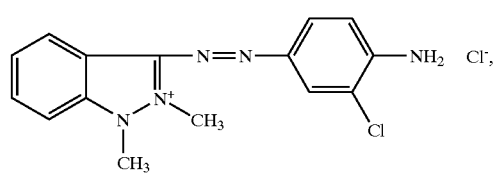 (V36)
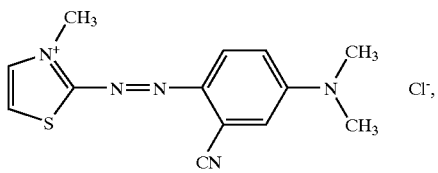 (V45)
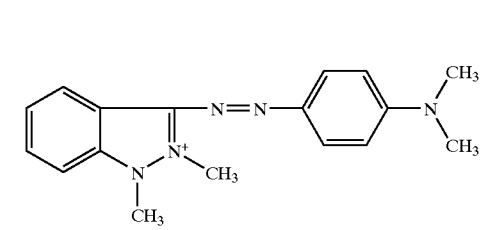 (V37)
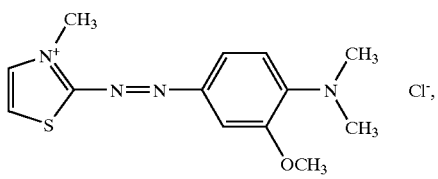 (V46)
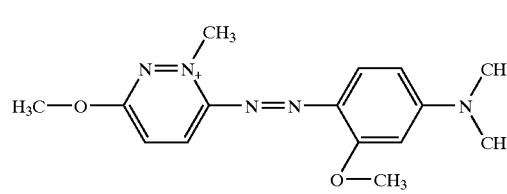 (V38)
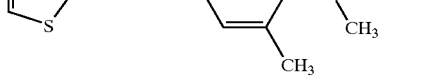 (V47)
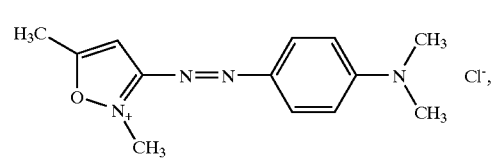 (V39)
 (V48)
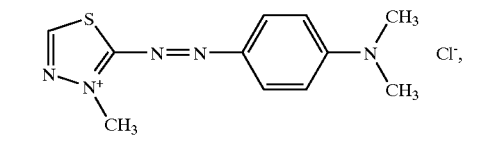 (V40)
 (V49)
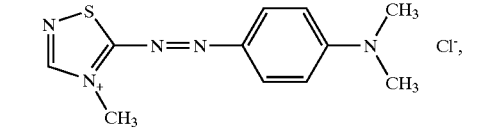 (V41)
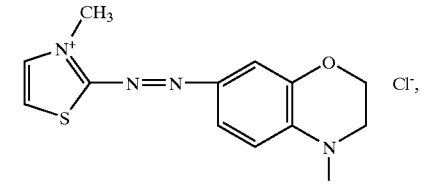 (V50)
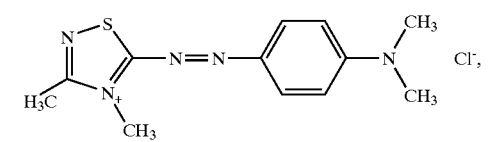 (V42)
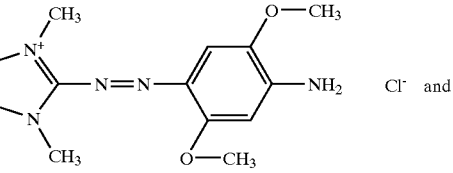 (V51)
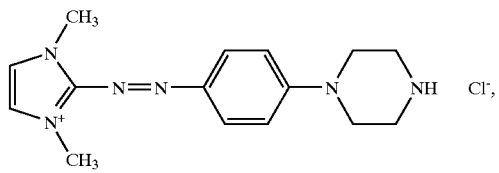 (V43)
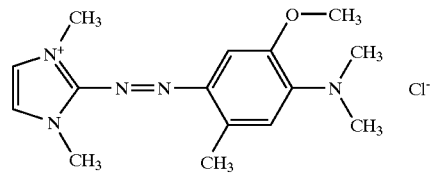 (V52)
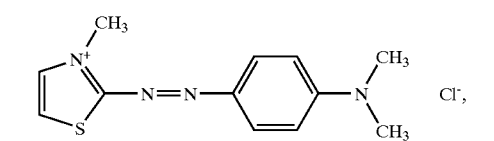 (V44)
Among the above compounds with the structures (V1) to (V52), the compounds with the structures (V1), (V2), (V4), (V14) and (V31) are particularly preferred.
Among the cationic direct dyes of the formula (VI), which are applicable in the ready-to-use dye compositions according to the invention, the compounds with the following structures (VI1) to (VI12) can in particular be mentioned:

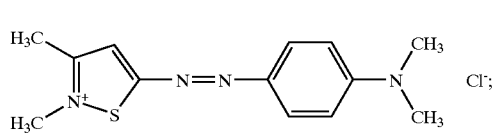 (VI1)

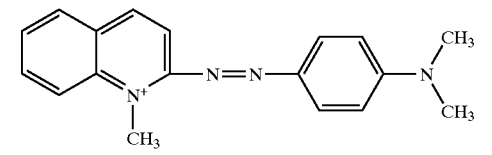 (VI2)

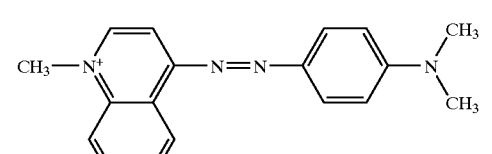 (VI3)

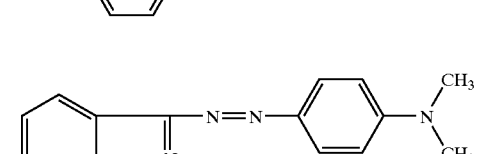 (VI4)

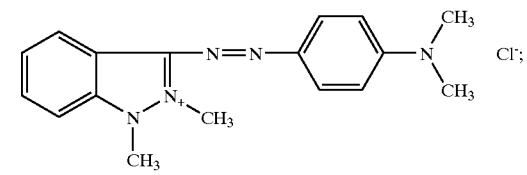 (VI5)

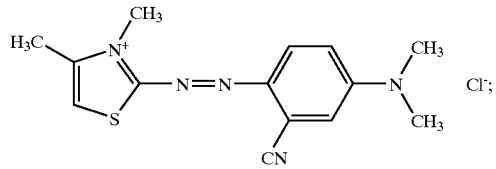 (VI6)

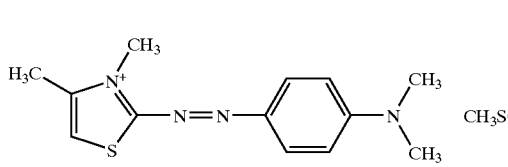 (VI7)

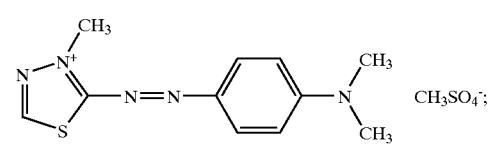 (VI8)

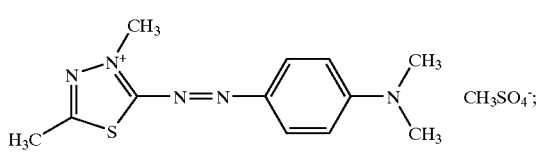 (VI9)

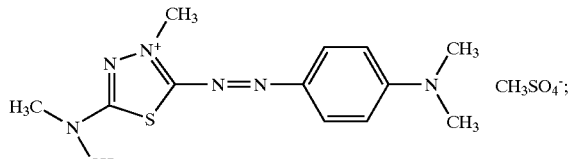 (VI10)

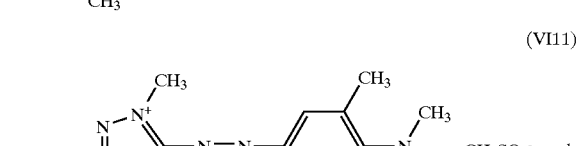 (VI11)

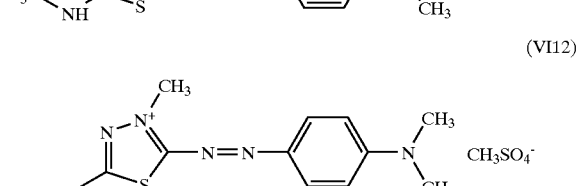 (VI12)

Among the cationic direct dyes of the formula (VII), which are applicable in the ready-to-use dye compositions according to the invention, the compounds with the following structures (VII1) to (VII18) can in particular be mentioned:

(VII1)

(VII2)

(VII3)

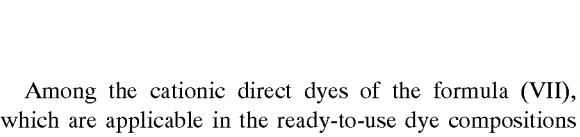 (VII4)

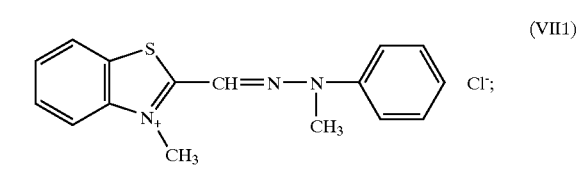 (VII5)

Among the above particular compositions with the structures (VII1) to (VII18), the compounds with the structures (VII4), (VII5) and (VII13) are particularly preferred.

Among the cationic direct dyes of the formula (VII'), which are applicable in the ready-to-use dye compositions according to the invention, the compounds with the following structures (VII'1) to (VII'3) can in particular be mentioned:

The cationic direct dye or dyes used according to the invention represent preferably between approximately 0.001% and approximately 10% by weight of the total weight of the ready-to-use dye composition, especially between approximately 0.05% and approximately 5% by weight.

In general, the acid addition salts suitable within the scope of the dye compositions according to the invention (oxidation bases and coupling agents) are especially selected from hydrochlorides, hydrobromides, sulphates, tartrates, lactates and acetates.

With regard to laccase which is an oxidase used in the present invention, there is no particular limitation for its source, etc. but those derived from microorganisms are preferred. Among them, laccase derived from genus Myceliophthora or Scytalidium is preferred. The compounding amount of laccase in the composition of the present invention varies depending upon dosage form, frequency and treating time of the preparation and upon titer of the enzyme preparation but, usually, it is 0.0005–20% or, preferably, 0.005–10%. When the amount is less than 0.0005%, a sufficient effect is not resulted while, even when it is more than 20%, an increase in the effect proportional to the increase of the amount is not achieved.

Particularly preferred enzymes are laccases and related enzymes, the term "laccases and related enzymes" including enzymes comprised by the enzyme classification E. C. 1.10.3.2 (laccases) and catechol oxidase enzymes comprised by E. C. 1.10.3.1, bilirubin oxidase enzymes comprised by the enzyme classification E. C. 1.3.3.5 and mono-phenol mono-oxygenase enzymes comprised by the enzyme classification E. C. 1.14.99.1. Laccases are multi-copper containing enzymes that catalyze the oxidation of phenols and aromatic amines. Laccase-mediated oxidations result in the production of aryloxy-radical intermediates from suitable phenolic substrates; the ultimate coupling of the intermediates so produced provides a combination of dimeric, oligomeric, and polymeric reaction products.

The laccase may be derived from a microorganism, e.g. a fungus or a bacteria, or a plant. Preferably, the laccase employed is derived from a fungus. More preferably, it is derived from a strain of Polyporus sp., in particular a strain of *P. pinsitus* or *P. versicolor*, a strain of Myceliophthora sp., e.g. M. thermophila, a strain of Rhizoctonia sp., in particular a strain of Rh. praticola or Rh. solani, a strain of Pyricularia sp, in particular *P. oryzae*, or a strain of Scytalidium, such as *S. thermophilium*. The laccase may also be from a plant such as Rhus sp., e.g. *Rhus vernicifera*, In specific embodiments of the invention the oxidoreductase is a laccase such as a Polyporus sp. laccase, especially the *Polyporus pinisitus* laccase (also called *Trametes villosa* laccase) described in WO 96/00290 (from Novo Nordisk Biotec Inc.) or a Myceliophthora sp. laccase, especially the *Myceliophthora thermophila* laccase described in WO 95/33836 (from Novo Nordisk Biotech Inc.).

Further, the laccase may be a Scytalidium sp. laccase such as the *S. thermophilium* laccase described in WO 95/33837 and WO 97/19998 (from Novo Nordisk Biotech Inc.), the contents of which is incorporated herein by reference, or a Pyricularia sp. laccase, such as the *Pyricularia oryzae* laccase which can be purchased from SIGMA under the trade name SIGMA No. L5510, or a Coprinus sp. laccase, such as a *C. cinereus* laccase, especially a *C. cinereus* IFO 30116 laccase, or a Rhizoctonia sp. laccase, such as a *Rh. solani* laccase, especially the neutral *Rh. solani* laccase described in WO 95/07988 (from Novo Nordisk A/S) having a pH optimum in the range of from 6.0 to 8.5.

The laccase may also be derived from a fungus such as Collybia, Fomes, Lentinus, Pleurotus, Aspergillus, Neurospora, Podospora, Phlebia, e.g. *P. radiata* (WO 92/01046), Coriolus sp., e.g. *C. hirsitus* (JP 2–238885), or Botrytis.

Bilirubin oxidase may preferably be derived from a strain of Myrothecium sp., such as *M. verrucaria*.

Oxidases yielding peroxide ($H_2O_2$) are typically used in combination with a peroxidase to remove or at least reduce the peroxide produced.

Suitable oxidases include glucose oxidase (E. C. 1.1.3.4), hexose oxidase (E. C. 1.1.3.5), L-amino-acid oxidase (E. C. 1.4.3.2), xylitol oxidase, galactose oxidase (E. C. 1.1.3.9), pyranose oxidase (E. C. 1.1.3.10) and alcohol oxidase (E. C. 1.1.3.13).

If an L-amino acid oxidase is used, it may be derived from a Trichoderma sp. such as *Trichodezma harzianum*, such as the L-amino acid oxidase described in WO 94/25574 (from Novo Nordisk A/S), or *Trichodezma viride*.

A suitable glucose oxidase may originate from Aspergillus sp., such as a strain of *Aspergillus niger*, or from a strain of Cladosporium sp. in particular *Cladosporium oxysporum*.

Hexose oxidases from the red sea-weed *Chondrus crispus* (commonly known as Irish moss) (Sullivan and Ikawa, (1973), Biochim. Biophys. Acts, 309, p. 11–22; Ikawa, (1982), Meth. in Enzymol. 89, Carbohydrate Metabolism Part D, 145–149) oxidise a broad spectrum of carbohydrates, such as D-glucose, D-galactose, maltose, cellobiose, lactose, D-glucose 6-phosphate, D-mannose, 2-deoxy-D-glucose, 2-deoxy-D-galactose, D-fructose, D-glucuronic acid, and D-xylose.

Further, in addition to the above-mentioned components, it is also possible, if necessary, to add pH buffers, surface-active agents, thickeners such as hydroxyethyl cellulose and xanthan gum, perfumes, antiseptics, ultraviolet ray absorbers, antioxidants, bactericides, pearling agent, etc. With regard to the surface-active agents among the above, any of anionic ones such as α-olefinsulfonates, alkanesulfonates, fatty acid alkyl ether carboxylates, N-acylamino acids and $C_{12-18}$ saturated and unsaturated fatty acid acylglutamate esters; amphoteric ones such as alkylbetaines, alkylamidobetaines and hydroxysulfobetaines; cationic ones such as mono- or di-alkyl quaternary ammonium salts; and nonionic ones such as polyoxyethylene alkyl ethers and fatty acid alkylolamides may be used.

In order to improve the feel or touch of the hair, it is also possible to compound silicone derivatives such as dimethylpolysiloxane, amino-modified silicone and polyether-modified silicone.

The hairdye composition of the present invention may be prepared into any of dosage forms of liquid, cream, gel, aerosol, etc. and, in that case, it is preferred to prepare into a single preparation type in view of usability, etc.

In the preparation of the composition by compounding the above-mentioned components, it is preferred that the compounding is carried out in vacua or in an atmosphere of inert gas such as nitrogen gas, carbon dioxide gas or rare gas. With regard to a method for compounding, any method will do and there is no particular limitation therefor. Examples are a method where vacuation is conducted, a method where substitution with nitrogen gas is conducted and a method where vacuation is conducted followed by substituting with inert gas.

It is particularly preferred that the composition of the present invention is made into a form of aerosol and, when made into an aerosol form, it is preferred to carry out a shaking operation during and/or immediately after charging a propellant. This is an operation whereby the residual oxygen in a container is compulsorily consumed and formation of a dye precursor is suppressed. Thus, by such an operation, insolubilization and aggregation of the dye in the system do not occur whereby stability becomes good. Method for the shaking may be any of means of up-and-down, horizontal, turning and the shape of the FIG. 8 and there is no particular limitation therefor. Time for shaking may be dependent upon the type and is from 10 seconds to 30 minutes or, preferably, 1–10 minute(s).

The propellant may be any of liquefied propane gas (LPG), dimethyl ether (DME), nitrogen gas, carbon dioxide gas, etc. and, in view of production of foams after spraying, LPG is preferred.

Charging of the propellant may be carried out in air although it is preferred to charge in vacuo or in an atmosphere of inert gas such as nitrogen gas, carbon dioxide gas and rare gas. With regard to a method therefor, any method will do and there is no particular limitation.

The pH of the hairdye composition of the present invention is preferably 5.0–9.5 or, more preferably, 6.0–8.0. When the pH is higher than 9.5, there may be a case where a problem of irritation occurs.

EXAMPLES

The present invention will now be specifically illustrated by way of the following Examples and Comparative Examples although the present invention is not limited thereto. In the following examples, % means that by weight. Methods for testing the properties used in the following examples are as follows.

Skin Irritation:

The test was carried out according to a method by Kimber, et al (Toxicol. Lett., 55:203–213, 1991) and Hostineck, et al. (Arch. Dermatol. Res., 287:567–571, 1995) which have been used as animal substitution methods for the evaluation of sensitivity. Thus, a developer substance was dissolved in a mixture of acetone and olive oil (in a mixing ratio of 4:1) to an extent of 2% and the solution was applied to skin of the back of a Balb/c mouse of eight weeks age. After five days from the application, lymph node was taken out from the treated mouse and then lymphoid cells were suspended in a PRMI 1640 medium to which autoserum was added whereupon a lymphoid cell solution was prepared.

The resulting lymphoid cells were incubated at 37° C. for three days in the presence of 5% of $CO_2$ and the growing activity of the incubated solution was measured. Degree of sensitivity was judged by calculating the sensitivity index from the following formula followed by referring to the following criteria.

Sensitivity Index=(Growing Activity of Lymphoid Cells of Mice Applied with the Substance to be Evaluated)/(Growing Activity of Lymphoid Cells of Mouse Applied with Acetone-Olive Oil Mixture)

| | Sensitivity Degree | Sensitivity Index |
|---|---|---|
| ○○ | very weak | 1.0 or more but less than 1.25 |
| ○ | weak | 1.25 or more but less than 1.5 |
| Δ | somewhat weak | 1.5 or more but less than 1.75 |
| x | strong | 1.75 or more |

Hair-dying Property (ΔE):

About 10 g of a dried tuft of white hair of goat were shampooed, water was removed therefrom (weight of the tuft after removing the water was 17 g) and each 3 g of the compositions to be evaluated (the products immediately after the compounding) were applied thereto quickly and uniformly. This was allowed to stand at 30° C. for a predetermined period, rinsed, dried, shampooed and air-dried and a hair-dyeing property to the hair of goat was evaluated.

With regard to the hair-dyeing property (ΔE), the L, a and b values of the dyed tuft were measured by a color difference meter (SE2000 manufactured by Nippon Denshoku) and the color difference (ΔE) from the hair which was not dyed was calculated whereby the hair-dyeing property was evaluated. Incidentally, the more the ΔE, the better the hair dyeing property.

EXAMPLES AND COMPARATIVE EXAMPLES

A hairdye composition of a single preparation type having the following formulation was prepared and its properties were evaluated. The result is shown in Table 2.

| Compounded Components | Amount (%) |
|---|---|
| Example 1 (Gel Type) | |
| 5,6-Dihydroxyindoline.HBr | 3 |
| Laccase (from genus Myceliophthora) | 0.5 |
| Xanthan gum | 0.5 |
| Hydroxyethyl cellulose | 0.5 |
| Ethanol | 5.0 |
| Pure water | balance |
| Total | 100.0 |
| pH (as adjusted by NaOH) | 7.0 |
| Example 2 (Gel Type) | |
| 5,6-Dihydroxyindoline.HBr | 2 |
| Toluene-2,5-diamine sulfate | 0.01 |
| p-Aminophenol | 0.01 |
| Laccase (from genus Scytalidium) | 0.5 |
| Xanthan gum | 0.5 |
| Hydroxyethyl cellulose | 0.5 |
| Ethanol | 5.0 |
| Pure water | balance |
| Total | 100.0 |
| pH (as adjusted by NaOH) | 7.0 |
| Comparative Example 1 (Gel Type) | |
| Toluene-2,5-diamine | 3 |
| p-Aminophenol | 1 |
| Laccase (from genus Myceliophthora) | 0.5 |
| Xanthan gum | 0.5 |
| Hydroxyethyl cellulose | 0.5 |
| Ethanol | 5.0 |
| Pure water | balance |
| Total | 100.0 |
| pH (as adjusted by NaOH) | 7.0 |
| Example 3 (Cream Type) | |
| 5,6-Dihydroxyindoline.HBr | 3 |
| Decaglyceryl monostearate | 3 |
| Cetostearyl alcohol | 0.5 |
| Stearic acid | 0.8 |
| Xanthan gum | 1 |
| Laccase (from genus Myceliophthora) | 1 |
| Carboxymethyl cellulose | 1 |
| Sodium hydroxide | q.s. |
| Pure water | balance |
| Total | 100.0 |
| pH (as adjusted by NaOH) | 7.0 |
| Example 4 (Cream Type) | |
| 5,6-Dihydroxyindoline.HBr | 3 |
| POE(10) Cetyl ether | 8 |
| Stearyl alcohol | 2.5 |
| Oleyl alcohol | 5 |
| Behenyl alcohol | 2 |
| Cetyl alcohol | 2 |
| Stearyltrimethylammonium chloride | 1 |
| Laccase (from Japanese lacquer tree) | 1 |
| Glycerol | 2 |
| Triethanolamine | q.s. |
| Pure water | balance |
| Total | 100.0 |
| pH (as adjusted by NaOH) | 7.0 |
| Comparative Example 2 (Cream Type) | |
| Toluene-2,5-diamine sulfate | 3 |
| p-Aminophenol | 1 |
| Decaglyceryl monostearate | 3 |
| Cetostearyl alcohol | 0.5 |
| Stearic acid | 0.8 |
| Laccase (from genus Myceliophthora) | 1 |
| Carboxymethyl cellulose | 1 |

-continued

| Compounded Components | Amount (%) |
|---|---|
| Sodium hydroxide | q.s. |
| Pure water | balance |
| Total | 100.0 |
| pH (as adjusted by NaOH) | 7.0 |

TABLE 1

(Aerosol Type)

| Components (%) | Examples | | | | | | | Comp. Ex.s | | |
|---|---|---|---|---|---|---|---|---|---|---|
| | 5 | 6 | 7 | 8 | 9 | 10 | 11 | 3 | 4 | 5 |
| 5,6-Dihydroxyindoline.HBr | 3 | 2 | 3 | 1 | 2 | 2 | 1.5 | — | — | — |
| Toluene-5,6-diamine sulfate | — | — | — | — | — | 0.01 | — | 3 | 3 | 3 |
| p-Aminophenol | — | — | — | — | — | 0.01 | 0.01 | 2 | 1 | 2 |
| m-Phenylenediamine | — | — | — | — | — | — | 0.01 | — | 0.5 | — |
| Resorcinol | — | — | — | — | — | — | 0.01 | 0.5 | 1 | 0.5 |
| Ethanol | 5 | 5 | 5 | 5 | 5 | 5 | 5 | 5 | 5 | 5 |
| POE Lauryl ether sodium sulfate | 0.3 | 0.3 | 0.3 | 0.3 | 0.3 | 0.3 | 0.3 | 0.3 | 0.3 | 0.3 |
| Coconut oil fatty acid diethanolamide | 0.2 | 0.2 | 0.2 | 0.2 | 0.2 | 0.2 | 0.2 | 0.2 | 0.2 | 0.2 |
| Laccase (genus Myceliophthora) | 0.5 | 0.05 | — | 1 | — | 0.5 | — | 0.5 | — | — |
| Laccase (genus Scytalidium) | — | — | 1 | — | 0.5 | — | 0.5 | — | — | 0.5 |
| Sodium hydroxide | q.s. | q.s. | q.s. | q.s. | q.s. | q.s. | q.s. | q.s. | q.s | q.s |
| LPG (4 kg/cm$^2$) | 4 | 4 | 4 | 4 | 4 | 4 | 4 | 4 | 4 | 4 |
| Pure water | b | b | b | b | b | b | b | b | b | b |
| Total | 100.0 | 100.0 | 100.0 | 100.0 | 100.0 | 100.0 | 100.0 | 100.0 | 100.0 | 100.0 |
| pH | 7.0 | 7.0 | 7.0 | 7.0 | 7.0 | 7.0 | 7.0 | 7.0 | 7.0 | 7.0 | b balance

TABLE 2

| | Examples | | | | | | | | | | | Comp.Ex. | | | | |
|---|---|---|---|---|---|---|---|---|---|---|---|---|---|---|---|---|
| | 1 | 2 | 3 | 4 | 5 | 6 | 7 | 8 | 9 | 10 | 11 | 1 | 2 | 3 | 4 | 5 |
| Skin Irritation | oo | o | oo | oo | oo | oo | oo | oo | oo | o | o | x | x | x | x | x |
| Dyeing Prop(ΔE) | 28 | 30 | 29 | 27 | 31 | 28 | 30 | 27 | 28 | 30 | 29 | 31 | 29 | 30 | 14 | 28 |

A hairdye composition of the present invention exhibits little skin irritation and has an excellent hair dyeing effect.

What is claimed is:

1. A hair dye composition in the form of an aerosol of one-pack type comprising:
   5,6-dihydroxyindoline or its salt;
   a laccase;
   water; and
   a propellant;
   wherein said hair dye composition has a pH of 5.0 to 9.5, and
   a shaking operation is carried out during, immediately, or during and immediately after charging the propellant so that the residual oxygen is consumed and the formation of a dye precursor is suppressed.

2. The hair dye composition of claim 1, said hair dye composition further comprising at least one more indoline or indoline compound.

3. The hair dye composition of claim 1, wherein the concentration of said 5,6-dihydroxyindoline or its salt is 0.01–30% by weight of said hair dye composition.

4. The hair dye composition of claim 1, further comprising an oxidation dye selected from the group consisting of 5-amino-o-cresol, o-aminophenol, m-aminophenol, p-aminophenol, 2,6-diaminopyridine, 5-(2-hydroxylethylamino)-2-methylphenol, N,N-bis(β-hydroxyl)-p-phenylenediamine sulfate, p-nitro-o-phenylenediamine, p-phenylenediamine, m-phenylenediamine, N-phenyl-p-phenylenediamine, resorcinol, 2-hydroxyl-5-nitro-2',4'-diaminoazobenzene sodium sulfate, toluene-2,5-diamine, 5-amino-o-cresol sulfate, p-aminophenol sulfate, o-chloro-p-phenylenediamine sulfate, 4,4'-diaminodiphenylamine sulfate, p-methylaminophenol sulfate, p-phenylenediamine sulfate, m-phenylenediamine sulfate, toluene-2,5-diamine sulfate, 2,4-diaminophenoxyethanol hydrochloride, toluene-2,5-diamine hydrochloride, m-phenylenediamine hydrochloride, 2,4-diamrinophenol hydrochloride, 3,3'-iminodiphenol, p-phenylenediamine hydrochloride, N-phenyl-p-phenylenediamine hydrochloride, N-phenyl-p-phenylenediamine acetate, 1,5-dihydroxynaphthalene, toluene-3,4-diamine, p-methylaminophenol, N,N'-bis(4-aminophenyl)-2,5-diamino-1,4-quinonediimine, o-aminophenol sulfate, 2,4-diaminophenyl sulfate and m-aminophenol sulfate.

5. The hair dye composition of claim 1, further comprising an oxidation base selected from the group consisting of a para-phenylenediamine, a double base, a para-aminophenol, an ortho-aminophenol and a heterocyclic oxidation base.

6. The hair dye composition of claim 5, wherein said para-phenylenediamine as the oxidation base is selected from the group consisting of para-phenylenediamine, paratoluylenediamine, 2-isopropyl para-phenylenediamine, 2-0-hydroxyethyl para-phenylenediamine, 2-β-hydroxyethyloxy para-phenylenediamine, 2,6-dimethyl para-phenylenediamine, 2,6-diethyl para-phenylenediamine, 2,3-dimethyl para-phenylenediamine, N,N-bis-(β-hydroxyethyl) para-phenylenediamine, 2-chloro para-phenylenediamine, 2-β-acetylaminoethyloxy para-phenylenediamine and acid addition salts thereof.

7. The hair dye composition of claim 5, wherein said double base as the oxidation base is selected from the group consisting of N,N=-bis-(β-hydroxyethyl) N,N'-bis-(4'-aminophenyl) 1,3-diamino propanol, N,N=-bis-(β-hydroxyethyl) N,N=-bis-(4'-aminophenyl) ethylenediamine, N,N=-bis-(4-aminophenyl) tetramethylenediamine, N,N'-bis-(β-hydroxyethyl) N,N'-bis-(4-aminophenyl) tetramethylenediamine, N,N'-bis-(4-methylaminophenyl) tetramethylenediamine, N,N'-bis-(ethyl) N,N'-bis-(4'-amino, 3-methylphenyl) ethylenediamine, 1,8-bis-(2,5-diaminophenoxy)-3,5-dioxaoctane and acid addition salts thereof.

8. The hair dye composition of claim 5, wherein said para-aminophenol as the oxidation base is selected from the group consisting of para-aminophenol, 4-amino 3-methyl phenol, 4-amino 3-fluoro phenol, 4-amino 3-hydroxymethyl phenol, 4-amino 2-methyl phenol, 4-amino 2-hydroxymethyl phenol, 4-amino 2-methoxymethyl phenol, 4-amino 2-aminomethyl phenol, 4-amino 2-(β-hydroxyethyl aminomethyl) phenol, 4-amino 2-fluoro phenol and acid addition salts thereof.

9. The hair dye composition of claim 5, wherein said ortho-aminophenol as the oxidation base is selected from the group consisting of 2-amino phenol, 2-amino 5-methyl phenol, 2-amino 6-methyl phenol, 5-acetamido 2-amino phenol and acid addition salts thereof.

10. The hair dye composition of claim 5, wherein said heterocyclic oxidation base is selected from the group consisting of pyridine derivatives, pyrimidine derivatives, pyrazole derivatives, pyrazolo-pyrimidine derivatives and acid addition salts thereof.

11. The hair dye composition of claim 5, wherein said oxidation base or bases is 0.0005% to 12% by weight of said hair dye composition.

12. The hair dye composition of claim 1, further comprising a coupling agent selected from the group consisting of 2-methyl-5-amino-phenol, 5-N-(β-hydroxyethyl)-amino-2-methyl-phenol, 3-amino-phenol, 1,3-dihydroxybenzene, 1,3-dihydroxy-2-methyl-benzene, 4-chloro-1,3-dihydroxybenzene, 2,4-diamino-1-(β-hydroxyethyloxy)-benzene, 2-amino-4-(β-hydroxyethylamino)-1-methoxy-benzene, 1,3-diamino-benzene, 1,3-bis-(2,4-diaminophenoxy)-propane, sesamol, α-naphtol, 6-hydroxy-indole, 4-hydroxy-indole, 4-hydroxy-N-methyl-indole, 6-hydroxy-indolin, 2,6-dihydroxy-4-methyl-pyridine, 1-H-3-methyl-pyrazole-5-on, 1-phenyl-3-methyl-pyrazole-5-one, 2,6-dimethyl-1,2,4-triazole, 2,6-dimethyl-1,2,4-triazole, 6-methyl-pyrazolo-benzimidazole and acid addition salts thereof.

13. The hair dye composition of claim 12, wherein said coupling agent or agents is 0.0001% to 10% by weight of said hair dye composition.

14. The hair dye composition of claim 1, further comprising a cationic direct dye.

15. The hair dye composition of claim 1, wherein said laccase is 0.0005 to 20% by weight of said hair dye composition.

16. The hair dye composition of claim 1, further comprising at least one ingredient selected from the group consisting of a pH buffer, a surface-active agent, a thickener, a perfume, an antiseptic, an ultraviolet ray absorber, an antioxidant, a bactericide, a pearling agent and a silicone derivative.

17. The hair dye composition of claim 1, wherein said pH is 6.0 to 8.0.

18. A method of making a hair dye composition in the form of am erosol of one-pack type comprising:
   preparing said hair dye composition by compounding a composition comprising 5,6-dihydroxyindoline or its salt, laccase, and water;
   placing said hair dye composition in a container;
   charging a propellant in said container in vacuo or in an atmosphere of inert gas to form an aerosol of one-pack type; and
   shaking said aerosol of one-pack type during, immediately, or during and immediately after charging the propellant, wherein said shaking consumes the residual oxygen and suppresses the formation of a dye precursor in said aerosol of one-pack type.

19. The hair dye composition of claim 1, wherein said laccase is derived from a microorganism.

20. The hair dye composition of claim 19, wherein said laccase is derived from a fungus.

21. The hair dye composition of claim 20, wherein said laccase is derived from a strain of Polyporus sp.

* * * * *